US007858360B2

(12) United States Patent
Hansen et al.

(10) Patent No.: US 7,858,360 B2
(45) Date of Patent: Dec. 28, 2010

(54) USE OF FUNGAL MUTANTS FOR EXPRESSION OF ANTIBODIES

(75) Inventors: Mogens Trier Hansen, Lynge (DK); Christian Isak Jorgensen, Bagsvaerd (DK); Jan Lehmbeck, Vekso (DK)

(73) Assignee: Novozymes A/S, Bagsvaerd (DK)

( * ) Notice: Subject to any disclaimer, the term of this patent is extended or adjusted under 35 U.S.C. 154(b) by 462 days.

(21) Appl. No.: 12/065,924

(22) PCT Filed: Oct. 17, 2006

(86) PCT No.: PCT/DK2006/000586

§ 371 (c)(1),
(2), (4) Date: Mar. 6, 2008

(87) PCT Pub. No.: WO2007/045248

PCT Pub. Date: Apr. 26, 2007

(65) Prior Publication Data

US 2008/0248530 A1 Oct. 9, 2008

Related U.S. Application Data

(60) Provisional application No. 60/728,953, filed on Oct. 20, 2005.

(30) Foreign Application Priority Data

Oct. 17, 2005 (DK) ............................... 2005 01452

(51) Int. Cl.
*C12N 1/15* (2006.01)
*C12N 15/80* (2006.01)
(52) U.S. Cl. ............... 435/254.11; 435/69.1; 435/254.3
(58) Field of Classification Search ....................... None
See application file for complete search history.

(56) References Cited

U.S. PATENT DOCUMENTS

| 6,013,452 A * | 1/2000 | Christensen et al. ........... 435/6 |
| 2005/0158825 A1 * | 7/2005 | Power et al. ............... 435/69.1 |

FOREIGN PATENT DOCUMENTS

| EP | 0574347 | 12/1993 |
| WO | WO 90/00192 | 1/1990 |
| WO | WO 97/22705 | 6/1997 |
| WO | WO 98/12300 | 3/1998 |

OTHER PUBLICATIONS

Tatsumi, H., et al., 1989, "A full length cDNA clone for the alkaline protease from *Aspergillus oryzae*: Structural analysis and expression in *Saccharomyces cerevisiae*", Molecular and General Genetics, vol. 219, No. 1, pp. 33-38.*
Murakami, K., et al., 1991, "Isolation and characterization of the alkaline protease gene of *Aspergillus oryzae*", Agricultural and Biological Chemistry, vol. 55, No. 11, pp. 2807-2811.*
Frederick, G. D., et al., 1993, "Cloning and characterisation of pepC, a gene encoding a serine protease from *Aspergillus niger*", Gene, vol. 125, No. 1, pp. 57-64.*
Jaton-Ogay, K., et al., 1994, "Cloning and disruption of the gene encoding an extracellular metalloprotease of *Aspergillus fumigatus*", Molecular Microbiology, vol. 14, No. 5, pp. 917-928.*
Yu, C.-J., et al., 1999, "Characterization of a novel allergen, a major IgE-binding protein from *Aspergillus flavus*, as an aklaline serine protease", Biochemical and Biophysical Research Communications, vol. 261, pp. 669-675.*
Blinkovsky, A. M., et al., 2000, "A non-specific aminopeptidase from *Aspergillus*", Biochimica et Biophysica Acta, vol. 1480, pp. 171-181.*
Jousson, O., et al., 2004, "Multiplication of an ancestral gene encoding secreted fungalysin preceded species differentiation in the dermatophytes Trichophyton and Microsporum", Microbiology, vol. 150, pp. 301-310.*
Machida, M., et al., 2005, "Genome sequencing and analysis of *Aspergillus oryzae*", Nature, vol. 438, No. 22, pp. 1157-1161.*
Punt et al., "The role of the *Aspergillus niger* furin-type protease gene in processing of fungal proproteins and fusion proteins. Evidence for alternative processing of recombinant (fusion-) proteins", Journal of Biotechnology, vol. 106, No. 1, pp. 23-32 (2003).
Hombergh Van Den et al., "New protease mutants in *Aspergillus niger* result in strongly reducted in vitro degradation of target proteins", Current Genetics, vol. 28, No. 4, pp. 299-308 (1995).
Hombergh Van Den et al., "Production of the homologous pectin lyase B protein in six genetically defined protease-deficient *Aspergillus niger* mutant strains", Current Genetics, vol. 32, No. 1, pp. 73-81 (1997).
Frederick et al., "Cloning and characterization of pepC, a gene encoding a Serine protease from *Aspergillus niger*", Gene, vol. 125, pp. 57-64 (1993).
Jalving et al., "Characterization of the Kexin-Like Maturase of *Aspergillus niger*". Applied and Environmental Microbiology, vol. 66, pp. 363-368 (2000).
Kwon et at., "Molecular cloning of kpcA Gene Encoding Kex2p-like Endoprotease from *Aspergillus nidulans*" Molecular Cell. vol. 12, pp. 142-147 (2001).
Mizutani et al., "Disorder cell Integrity signaling caused by disruption of the kexB gene in *Aspergillus oryzae*" Eukaryotic Cell, vol. 31, pp. 1036-1048 (2004).

* cited by examiner

*Primary Examiner*—Nashaat T Nashed
*Assistant Examiner*—William W Moore
(74) *Attorney, Agent, or Firm*—Michael W. Krenicky

(57) ABSTRACT

The disclosure relates to a filamentous fungal cell in which an endogenous alkaline protease activity, an endogenous neutral metalloprotease activity, an endogenous serine protease activity, and an endogenous kexin maturase activity have been completely or partially inactivated. Particularly the endogenous alkaline protease activity, the endogenous.neutral metalloprotease activity, the endogenous serine protease activity, and the kexin maturase activity are encoded by the alp, npI, pepC and kexB genes respectively. The filamentous fungal cell is particularly suitable for production of heterologous proteins such as antibodies.

10 Claims, No Drawings

SEQUENCE LISTING

<160> NUMBER OF SEQ ID NOS: 33

<210> SEQ ID NO 1
<211> LENGTH: 23
<212> TYPE: DNA
<213> ORGANISM: Artificial
<220> FEATURE:
<223> OTHER INFORMATION: PCR primer

<400> SEQUENCE: 1
cattaccctc ttaccgccat acc                                          23

<210> SEQ ID NO 2
<211> LENGTH: 46
<212> TYPE: DNA
<213> ORGANISM: Artificial
<220> FEATURE:
<223> OTHER INFORMATION: Pcr primer

<400> SEQUENCE: 2
cgctagcaag actcgagaag agggaaaatc aagttagacc aagggc        46

<210> SEQ ID NO 3
<211> LENGTH: 41
<212> TYPE: DNA
<213> ORGANISM: Artificial
<220> FEATURE:
<223> OTHER INFORMATION: PCR primer

<400> SEQUENCE: 3
cctcttctcg agtcttgcta gcgtttatgg cagggtatgg g        41

<210> SEQ ID NO 4
<211> LENGTH: 23
<212> TYPE: DNA
<213> ORGANISM: Artificial
<220> FEATURE:
<223> OTHER INFORMATION: PCR primer

<400> SEQUENCE: 4
gattcatgtg actgaacgta ccg        23

<210> SEQ ID NO 5
<211> LENGTH: 35
<212> TYPE: DNA
<213> ORGANISM: Artificial
<220> FEATURE:
<223> OTHER INFORMATION: PCR primer

<400> SEQUENCE: 5
cctgaattca cgcgcgccaa catgtcttcc aagtc        35

<210> SEQ ID NO 6
<211> LENGTH: 18
<212> TYPE: DNA
<213> ORGANISM: Artificial
<220> FEATURE:
<223> OTHER INFORMATION: PCR primer

<400> SEQUENCE: 6
accatggcgg cactctgc        18

<210> SEQ ID NO 7
<211> LENGTH: 31
<212> TYPE: DNA
<213> ORGANISM: Artificial
<220> FEATURE:
<223> OTHER INFORMATION: PCR primer

<400> SEQUENCE: 7
gttctcgagc tacttattgc gcaccaacac g        31

<210> SEQ ID NO 8
<211> LENGTH: 18
<212> TYPE: DNA
<213> ORGANISM: Artificial
<220> FEATURE:
<223> OTHER INFORMATION: PCR primer

<400> SEQUENCE: 8
gagccgtagg ggaagtcc        18

<210> SEQ ID NO 9
<211> LENGTH: 19
<212> TYPE: DNA
<213> ORGANISM: Artificial

-continued

```
<220> FEATURE:
<223> OTHER INFORMATION: PCR primer

<400> SEQUENCE: 9
cttcagactg aacctcgcc                                              19

<210> SEQ ID NO 10
<211> LENGTH: 20
<212> TYPE: DNA
<213> ORGANISM: Artificial
<220> FEATURE:
<223> OTHER INFORMATION: PCR primer

<400> SEQUENCE: 10
gactcggtcc gtacattgcc                                             20

<210> SEQ ID NO 11
<211> LENGTH: 38
<212> TYPE: DNA
<213> ORGANISM: Artificial
<220> FEATURE:
<223> OTHER INFORMATION: PCR primer

<400> SEQUENCE: 11
cctacggctc cgagagaggc cttttgatcc ttgcggag                         38

<210> SEQ ID NO 12
<211> LENGTH: 20
<212> TYPE: DNA
<213> ORGANISM: Artificial
<220> FEATURE:
<223> OTHER INFORMATION: PCR primer

<400> SEQUENCE: 12
gagttagtag ttggacatcc                                             20

<210> SEQ ID NO 13
<211> LENGTH: 37
<212> TYPE: DNA
<213> ORGANISM: Artificial
<220> FEATURE:
<223> OTHER INFORMATION: PCR primer

<400> SEQUENCE: 13
gacgacgaat tcaagcttat ggtgttttga tcatttt                          37

<210> SEQ ID NO 14
<211> LENGTH: 31
<212> TYPE: DNA
<213> ORGANISM: Artificial
<220> FEATURE:
<223> OTHER INFORMATION: PCR primer

<400> SEQUENCE: 14
gacgacgaat tcatacatcg catcgacaag g                                31

<210> SEQ ID NO 15
<211> LENGTH: 1410
<212> TYPE: DNA
<213> ORGANISM: Homo sapiens

<400> SEQUENCE: 15
atggagtttg tgctgagctg ggttttcctt gttgctatat taaaaggtgt ccagtgtgag    60
ggtcagctgg tgcaatctgg ggaggcttg gtacatcctg gggggtccct gagactctcc   120
```

```
tgtgcaggct ctggattcac cttcagtagc tatggtatgc actgggttcg ccaggctcca        180
ggaaaaggtc tggagtgggt atcaggtatt ggtactggtg gtggcacata ctctacagac        240
tccgtgaagg gccgattcac catctccaga gacaatgcca agaactcctt gtatcttcaa        300
atgaacagcc tgagagccga ggacatggct gtgtattact gtgcaagagg agattactat        360
ggttcgggga gtttctttga ctgctggggc cagggaaccc tggtcaccgt ctcctcagcc        420
tccaccaagg gcccatcggt cttccccctg gcacctcct ccaagagcac ctctgggggc         480
acagcggccc tgggctgcct ggtcaaggac tacttccccg aaccggtgac ggtgtcgtgg        540
aactcaggcg ccctgaccag cggcgtgcac accttcccgg ctgtcctaca gtcctcagga       600
ctctactccc tcagcagcgt ggtgaccgtg ccctccagca gcttgggcac ccagacctac        660
atctgcaacg tgaatcacaa gcccagcaac accaaggtgg acaagagagt tgagcccaaa       720
tcttgtgaca aaactcacac atgcccaccg tgcccagcac ctgaactcct gggggggaccg      780 tcagtcttcc tcttcccccc aaaacccaag gacaccctca tgatctcccg gacccctgag       840
gtcacatgcg tggtggtgga cgtgagccac gaagaccctg aggtcaagtt caactggtac       900
gtggacggcg tggaggtgca taatgccaag acaaagccgc gggaggagca gtacaacagc       960
acgtaccgtg tggtcagcgt cctcaccgtc ctgcaccagg actggctgaa tggcaaggag      1020
tacaagtgca aggtctccaa caaagccctc ccagccccca tcgagaaaac catctccaaa      1080
gccaaagggc agccccgaga accacaggtg tacaccctgc cccatcccg ggaggagatg       1140 accaagaacc aggtcagcct gacctgcctg gtcaaaggct tctatcccag cgacatcgcc      1200
gtggagtggg agagcaatgg gcagccggag aacaactaca agaccacgcc tcccgtgctg      1260
gactccgacg gctccttctt cctctatagc aagctcaccg tggacaagag caggtggcag      1320
caggggaacg tcttctcatg ctccgtgatg catgaggctc tgcacaacca ctacacgcag      1380
aagagcctct ccctgtcccc gggtaaatga                                       1410

<210> SEQ ID NO 16
<211> LENGTH: 27
<212> TYPE: DNA
<213> ORGANISM: Artificial
<220> FEATURE:
<223> OTHER INFORMATION: PCR primer

<400> SEQUENCE: 16
gacggatcca ccatggagtt tgtgctg                                            27

<210> SEQ ID NO 17
<211> LENGTH: 27
<212> TYPE: DNA
<213> ORGANISM: Artificial
<220> FEATURE:
<223> OTHER INFORMATION: PCR primer

<400> SEQUENCE: 17
gacctcgagt catttacccg gggacag                                            27

<210> SEQ ID NO 18
<211> LENGTH: 711
<212> TYPE: DNA
<213> ORGANISM: Homo sapiens

<400> SEQUENCE: 18
atggacatga gggtcctcgc tcagctcctg gggctcctgc tgctctgttt cccaggtgcc        60
agatgtgaca tccagatgac ccagtctcca tcctcactgt ctgcatctgt aggagacaga       120
```

```
gtcaccatca cttgtcgggc gagtcagggt attagcagct ggttagcctg gtatcagcag    180
aaaccagaga agcccctaa gtccctgatc tatgctgcat ccagtttgca aagtggggtc    240
ccatcaaggt tcagcggcag tggatctggg acagatttca ctctcaccat cagcagcctg    300
cagcctgaag attttgcaac ttattactgc aacagtata atagttaccc tcccactttt    360
ggccagggga ccaagctgga gatcaaacga actgtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata cgccctcca atcgggtaac    540 tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta g             711
```

<210> SEQ ID NO 19
<211> LENGTH: 28
<212> TYPE: DNA
<213> ORGANISM: Artificial
<220> FEATURE:
<223> OTHER INFORMATION: PCR primer

<400> SEQUENCE: 19
gacggatcca ccatggacat gagggtcc                                        28

<210> SEQ ID NO 20
<211> LENGTH: 28
<212> TYPE: DNA
<213> ORGANISM: Artificial
<220> FEATURE:
<223> OTHER INFORMATION: PCR primer

<400> SEQUENCE: 20
gacctcgagc taacactctc ccctgttg                                        28

<210> SEQ ID NO 21
<211> LENGTH: 60
<212> TYPE: DNA
<213> ORGANISM: Artificial
<220> FEATURE:
<223> OTHER INFORMATION: PCR primer

<400> SEQUENCE: 21
gacgaattct ctagaagatc tctcgaggag ctcaagcttc tgtacagtga ccggtgactc    60

<210> SEQ ID NO 22
<211> LENGTH: 27
<212> TYPE: DNA
<213> ORGANISM: Artificial
<220> FEATURE:
<223> OTHER INFORMATION: PCR primer

<400> SEQUENCE: 22
gacgaattcc gatgaatgtg tgtcctg                                         27

<210> SEQ ID NO 23
<211> LENGTH: 79
<212> TYPE: DNA
<213> ORGANISM: Artificial
<220> FEATURE:
<223> OTHER INFORMATION: PCR primer

<400> SEQUENCE: 23

```
gcacatatga tttaaatccc taatgttgac cctaatgttg accctaatgt tgagcggccg      60
cgtttaaacg aattcgccc                                                  79

<210> SEQ ID NO 24
<211> LENGTH: 71
<212> TYPE: DNA
<213> ORGANISM: Artificial
<220> FEATURE:
<223> OTHER INFORMATION: PCR primer

<400> SEQUENCE: 24
cgtaagctta tttaaatccc taatgttgac cctaatgttg accctaatgt tgagaccggt      60
gactctttct g                                                          71

<210> SEQ ID NO 25
<211> LENGTH: 6974
<212> TYPE: DNA
<213> ORGANISM: Aspergillus oryzae

<400> SEQUENCE: 25
gtcgacggcc cgggcggccg caaggggttc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg ccaagctatt     240
taggtgacac tatagaatac tcaagctttt gaagaggtga ccgatctgcc gcccaatcat     300
gcttttgctc tgccgtggag cgtaccgtgt tagagcgact caatggtgat tggtgactgt     360
ctctaggtga tgggaccata tgagggtcat ctcgcttcac cgaacttgag atagaaagtc     420
tagaatcagt tatgctgccc cgtgaagtag cgtactcatc gggtgaggca tatgactctg     480
gtggtaatgg cttttccatc cagttttgat gtccttcgca ggacaagtct ttggtcctcg     540
cggagaacga gcgagaagct tgatggccac gagctgcagc agggttgttc ttgtaggaca     600
ccgctcgagt ctgcgggaca tcgacagatc cgtaagtctg atcgctatca gtttcgtaat     660
ccaatgcggt aggtttcatg tcgtgagact gctgccgtcg gtgcgatggt gcgcgtggta     720
cactattcag agggacggat tggggaggta ttgagcctcc attagtaggc ctctgggagc     780
tagctgtagc catccttcaa agctcccgga ttcttcacga cacacactac ccagaaagct     840
tccgtacttt atcaccggta aaatcaaat gcgcggggaa tagaaaggtt agcgacacca      900
ataaagatcg taaagaaat caattcgtat ccaaatttat gatagtagca gatgatttga     960
ccagaccagt tcgtgttagt acatggtgat ggcactggaa gaataaatca tcgcttaatt    1020
cgcagagttg aaagttgcgg agtagtatac aagcgatgta gtatatggat tgtaacaagg    1080
gtggatttgt acagtatgag aggaaggtaa gatgatcgaa taccgcgatt tcaaccaggg    1140
gggaaaagaa tggaaaaaat taatgagatg acagaaaaat caacaggcta acaggattat    1200
attggagtga cgaattaatc tcattgtgct ggctaatgag aattaagtcg gtggctggca    1260
atggcgaacc agcacagttc catgcggggc tgactcgtca gtcatcctgc attaaacatg    1320
ctcccgccag gcaccacgac tggctcacgt tccccttttt ctaagaaaag aaattagcta    1380
ttagctttcg aaggagagga attatcggac taggagcatg aaagggtacc tggatagaaa    1440
acatgacgaa aagtatccat cgtgctgtgt cagtaatccg tgtataataa taagtagtac    1500
tgtagtcgtg ttgcagcagc tcaccgactg gatgcatccg ctggtgaatg agcaaatcat    1560
gaatgcaccg agtcagcatt gagcatagtc ggttttagta acattgtaaa gaagataatg    1620
```

```
gcattcttgt ttttgagaca tgtttcccat ccgctgtcca tcatgggatg tttcatttag    1680
attctccaat cggcggtgtg atcagtaatc ttatttcaac atctaccgta gattcaatgc    1740
tgcctcttag agcaattagt tacggttgtg aatgggccga gctgttgata taaaaagtaa    1800
ttccgagggg actgttgagg cattttgaaa attacggagc acatacatcg aaggggtat    1860 tgtatggacc gcgatctaga tctgcatacc gacttcgatt tcacaatgtt gattcgtcta    1920
ttgtagtcgt catctcattt tattgtacat acagtaagaa agggaaaact cagaataaga    1980
aaagaagtca ccaaaacagg gctgaatagt cctttcaact cttttttactt tttttttaggt    2040 tcttagtaac tgcctcccgt ccatgttact tagtatacgg agtactttc atatcatccc    2100 ttcacttgaa gtcagagggg ttttggctgt aaggagtaga ggcttagctg ctgataagtc    2160
aaggaaggta ctctgtacag tgcttattag aattttgcaa gaatgttcat ctagtcgaaa    2220
tctgagacgt ggggccaaaa tcttctagag tatgtactgt aattaattaa tatttagcac    2280
tgaatgaaaa ggctacctga gcactacgat ttaagtcagt ggagaacagg ttaaagttaa    2340
acaatgaatt tgtcgcctaa ggcaaaaggt tccgctgttt ccccgaagtg aacaccattc    2400
tcgaactccg cctccgcaac aacttcaccg agcagtgctc attgaataca taaccatttc    2460 ataccccct tgctgtttat attgcatatt tcttgtcttt atagtactct tttccttgaa    2520
gttgctttct gaatcgcaag ccatctactg aactgtctgg tactgttctt attgatggca    2580
actatcttat ttgtcctcat ctcgccttac tactgatagg agcctatctc gattcacgct    2640
actcccataa tgcggctttc cgaaagtgca acggtagcgt tcggcctttt ttgtgccgcg    2700
acggcatcag cccatcctcg acgctcctac gagacgcgcg atttctttgc tcttcatctt    2760
gacgattcca cctcccccaga cgagatcgcc caacgcctcg gagcacgcca cgagggtcaa    2820
gtaggtgaac tcacacaaca ccataccttc tctataccca aggagaacgg tgcagacctc    2880
gatgcgctgc tcgaacatgc acgaatcaga aaaaggtcaa gtcgtgccga aggacgtggc    2940
atgacgttgg acaaggaaag agatttgagt ggtatactct ggtctcaaaa gttagcccca    3000
aaacagcgac tagtaaagag ggctcctcca acaaatgtgg cgtcgagggg gtctgtgaaa    3060
gaagaggacc ccgtagctgc ccaagctcag aaacggattg cctcttcact tgggattaca    3120
gatcccattt tcggcggaca gtggcatctt tacaacactg tccaggttgg ccatgatctc    3180
aatgtttcgg acgtctggtt agaaggtatc accgggaaag gtgtcatcac ggctgtggtc    3240
gatgacggac tggacatgta cagcaacgac ctcaaaccga actactttgc tgagggctcc    3300
tacgatttta acgaccatgt accggagccc agaccgcggc ttggtgatga tagacacggc    3360
acaagatgtg ctggtgaaat tggagcagct aggaatgatg tctgtggagt aggcgttgca    3420
tacgacagcc aagttgccgg aattcggatt ttgtccgcac ccattgacga cgcagatgag    3480
gctgctgcca tcaactatgg cttcagcgc aatgatatat attcatgctc ttggggccct    3540
ccggatgatg cgccacgat ggaggcgcca gggattctta tcaaacgagc tatggttaac    3600
ggtatccaaa atggccgagg aggcaaaggt tctatttcg tctttgcagc tggaaatggt    3660
gcagggtacg atgacaactg caatttcgac ggctacacaa acagcattta cagcatcacc    3720
gtcggcgcta ttgatcgaga gggcaaacat cccagctact cggaatcatg ctctgcccag    3780
ttggttgtcg cttatagcag tggctcgagt gacgcgattc ataccactga cgttggaact    3840
gataaatgtt attcacttca cggcggaact tctgccgcag gccgctagc tgcgggtact    3900 attgccctcg ctcttagtgc ccgaccggaa ctaacttggc gagatgccca gtacctgatg    3960
```

```
atagagaccg cagttcccgt ccacgaagac gacgggagct ggcagactac caaaatgggg    4020
aagaagttta gccatgactg ggggtttggg aaagtagatg catattcact ggtacagctg    4080
gccaagacgt gggagctggt gaaaccacag gcgtggttcc actcaccgtg gctgcgggtg    4140
aagcatgaaa tcccacaagg tgaccagggt cttgccagct catacgaaat taccaaggat    4200
atgatgtatc aggccaatat cgagaaactg gaacatgtca ctgtgaccat gaatgtaaat    4260
cacactcgcc gaggcgacat cagtgtggag ttgcgcagcc ccgaaggtat cgtcagtcat    4320
ctgagtacag cgcggcggtc agataatgca aaggctggct atgaagactg gacgtttatg    4380
actgtggctc attggtatgt atttgctccc gtaatttagt tttcgttgtc agtcctgaca    4440
tttccattca ggggtgagtc cggtgttgga aagtggacgg tcattgtgaa ggataccaat    4500
gtcaatgatc atgttggaga attcatcgac tggcggctca acctctgggg actttcgatc    4560
gacggctcca gccagcccct tcatcctatg cccgatgagc atgacgatga ccactcgatt    4620
gaagatgcca ttgttgttac cactagtgtt gatcctctcc caactaagac tgaagcccca    4680
cctgtcccaa ctgatcccgt ggatcgtcct gtgaacgcaa agccatctgc gcagccaacg    4740
acgccttcag aggctcctgc tcaagagaca tctgaagctc ccaccccgac gaaacccagt    4800
tctactgaat caccttctac caccacctct gcggatagct ttttgccgtc cttcttcccc    4860
acgttcggcg cttcaaaacg gacccaggct tggatttacg ctgcgatcag ttcgatcatt    4920
gtattctgta ttggccttgg tgtctacttc cacgtacagc gacgaaagcg tctgcgtaat    4980
gatccgcgtg atgactacga tttcgaaatg atagaagatg aggatgaaac gcaggctatg    5040
aacgggcgtt cgggtcgtac acaacgccgg ggcggcgagc tttacaatgc tttcgctggg    5100
gagagcgacg aagaaccttt gtttagcgac gatgaggatg agccttatag ggatcatgcc    5160
cttagtgaag atcgggaacg gcgagggagc acaagtggtg accatgctcg gtcatagttt    5220
ggactaggct ttgcatttgc ttctacccta taatggtact ccttcggcgc gttcccgcta    5280
tatcagatga gatgtgttac atggatattg tgaattactg atgttgaacg aaggctgctg    5340
tatataattc tgacttgatt gacaaataga ctcataaagg acatgcatag gggtatcgta    5400
aatagctgca aagcgcgcta caagtaaaaa agtggatggg gttgatagag ttgctggata    5460
agccagtctt ggcgcttggg ccgatgacgc tggtgcggcc tcttctccaa ctgccgccat    5520
tgactgctcc actgctgcct ccgcaacttc tcaacctccc atttatcaat ctaccaccag    5580
caaccatagc tcctcatatc ccgaactacg ctatatctgg tctctccggt gatataaatt    5640
gcgtgcgagt ttcttttgac ttgtacaatt acctgtgtga agttgccgct tccctaacgg    5700 caaccccctcg atggatcagc acgatgactt tgacaatgtc tcatggagac acgaacctga    5760
gagcgacatc tctcgtccta ccacttcggg tactgatgcc gaagagtcgc ctgcgactag    5820
tcacgatgcc aatggcaagc ggagaatgag ctcagctcat gaaaacccac aagccgggcc    5880
actggcagat gcggtcgatc tagcaggtat cggggatggg gtgttggaat gccgggtgga    5940
ttcgcctctg aaagaaaatg acggtactaa agacgcatac atctcttatt tggttacaac    6000
acaagtgagt tgccccgttt ccccgggagt tacctgcggc ttgttcatgg cagtccactg    6060
tactgacggg agagacatcg cagaccgatt tcaagtcttt ccagaggtca gaatttgcag    6120
tgcgcagacg atttacggat tcttcttcc tatacaagac actctatcgg gaatatcctg    6180
cttgcgcggt cccacctcta cccgacaagc ataaaatgga atacgtacgg ggggatcggt    6240
tcgggcccga attcactaca cggcgtgcgt ggtcgctaca tcgatttcta aagcgcttgg    6300
cattacatcc ggtgcttcgc cgggctccct tgcttgctat attcctagaa tctcccgact    6360
```

-continued

```
ggaatgcgca tatgcggctt cacacttctc gcacatccac caatccgtcg gacaacagcg    6420
gtgcccccgg aattttttgac aactttaccg ataccttcgt aaatgcgttt acgaaagtcc   6480
acaagcctga tcgccggttc attgaggttc gagagaaggc agataaattg gatgaagatc    6540
tcaatcacgt agagaaaatc gtcgctaggg ttgctcggcg tgagtccgat ttagagaccg    6600
actataatga gctcgccaca caattccgca agttggtgtc tctggagcca aacgtcgagg    6660
ttcccctaca ggtattcgcg gcgtcggtgg aggagacggg acgtgggctc aaaggtctca    6720
aagatcacac ggatcaaaac taccttggct cgctccggga tatggaggcc tacattctgt    6780
ccctcaaggc gcttctaaaa acccgtgagc agaaacaact cgactttgaa gccctagtgg    6840
attaccgcaa caaagccgtg agcgagcgcg actcgctcgc caccaaccca tcatcctact    6900
atgcctctaa tccctgacc tcatcgcctg cgtccttcat ccgctccaag atggaagata    6960
tgcgcggggt cgac                                                     6974

<210> SEQ ID NO 26
<211> LENGTH: 1212
<212> TYPE: DNA
<213> ORGANISM: Aspergillus oryzae

<400> SEQUENCE: 26
atgcagtcca tcaagcgtac cttgctcctc ctcggagcta tccttcccgc ggtcctcggt      60
gcccctgtgc aggaaacccg ccgggccgct gagaagcttc ctggaaagta cattgtcaca    120
ttcaagcccg gcattgacga ggcaaagatt caggagcata ccacctgggc taccaacatt    180
caccagcgca gtctggagcg tcgtggcgcc actgcggtg atcttcctgt cggtattgag     240
cgcaactaca agatcaacaa gttcgccgcc tatgcaggct cttcgacga tgctaccatt    300 gaggagattc gcaagaacga agatgttgcc tacgtcgagg aggaccagat ctactacctc    360
gatggcctga ctacccagaa gagtgccccc tggggtctgg gcagcatttc ccacaagggc    420
cagcagagca ccgactacat ctacgacact agtgccggcg agggcaccta tgcctacgtg    480
gtggatagcg tgtcaatgt cgaccatgag gagttcgagg gccgcgccag caaggcctac    540
aacgctgccg gtggtcagca tgtggacagc attggccatg cacccacgt tccggcacc    600 attgctggca agacttatgg tatcgccaag aaggccagca tcctttcggt caaagttttc    660
cagggtgaat cgagcagcac ttccgtcatt cttgacggct tcaactgggc tgccaacgac    720
attgttagca agaagcgtac cagcaaggct gcaatcaaca tgagcttggg cggtggctac    780
tctaaggctt tcaacgatgc ggtcgagaac gcattcgagc agggtgttct ctcggttgtc    840
gctgccggta acgagaactc tgatgccggc caaaccagcc tgcctctgc ccctgatgcc    900 atcactgttg ccgctatcca gaagagcaac aaccgcgcca gtttctccaa ctttggcaag    960
gtcgttgacg tcttcgctcc cggtcaagat atcctttctg cctggattgg ctcttcctct   1020
gccaccaaca ccatctctgg tacctccatg gctactcccc acattgtcgg cctgtccctc   1080
tacctcgctg cccttgagaa cctcgatggc cccgctgccg tgaccaagcg catcaaggag   1140
ttggccacca aggacgtcgt caaggatgtt aagggcagcc taacctgct tgcctacaac   1200 ggtaacgctt aa                                                       1212

<210> SEQ ID NO 27
<211> LENGTH: 2071
<212> TYPE: DNA
<213> ORGANISM: Aspergillus oryzae
```

<400> SEQUENCE: 27

```
atgcggggtc ttctactagc tggagcccct tggcctacctt tggccgtcct tgcgcatccg    60
acccatcatg cacatggact tcaacgtcgc acagttgact tgaactcatt ccgtttgcac   120
caggcagcga agtatatcaa tgcgactgag tcttcgagtg atgtttcatc ttctttctct   180
cccttcaccg agcaaagcta cgtggagacg gccactcagc tcgtgaagaa tatcctgcca   240
gatgctacct tccgtgtcgt caaggatcat tacattggta gcaatggggt cgctcatgtc   300
aattttcgtc agacggtcca tggccttgac attgacaatg cggacttcaa tgtcaatgta   360
cgctgcagtc cacctatact atgttcggtg ctaaccactt catttaggtt gggaaaaatg   420
gaaagatctt ttcctatggc cactcatttt atacgggcaa atccccgat gccaatcctt    480
tgacgaagcg ggattatacc gaccctgtag cggctctcag aggaaccaac gaagctttac   540
agctttctat cactctagat caagtgtcta ctgaggctac cgaggacaaa gagtccttca   600
atttcaaggg agtctctggc accgtttcgg atcccaaggc tcagttggtc tacttggtaa   660
aggaagatgg cagccttgct ttgacctgga aggtggagac agatattgac agcaactggc   720
tgttgaccta catcgatgcc aataccggca agatgtcca tggtgtggtt gactacgtag    780
ccgaggcaga ttaccaagta tagtgagtat tttaagaatg tgacttggac tgtagaatga   840
agctgacaca ccaccacagt gcatggggta ttaatgatcc cacggagggc cctcgcaccg   900
tcatcagcga tccatgggat cgtccgcat ctgcgttcac ctggatcagt gacggagaaa    960
acaactatac acaactcgc ggcaacaacg gtatcgcgca gtcgaaccct accggtggat   1020
cgcagtactt gaagaactac cggcctgata gccccgattt gaaattccaa taccctatt    1080
cgctcaacgc cacaccccca gagtcctata ttgatgcgtc tatcactcag cttttctaca   1140
ctgccaacac gtaccacgac ctactctaca ctctgggctt caacgaggag gccggtaatt   1200
tccagtacga taacaatgga aaaggaggtg ctggaaacga ctacgtgatc ctcaatgctc   1260
aggacggttc tggcaccaat aacgccaact tcgctacgcc cccggatgga cagcccggcc   1320
gcatgcgcat gtacatttgg accgagtccc agccttaccg tgacggctcc ttcgaggctg   1380
gtattgtgat tcacgagtat actcacggtc tctctaaccg gctcactgga ggacctgcta   1440
actctcgctg cttgaatgcc cttgaatccg gcggaatggg tgaaggttgg ggagacttca   1500
tggccacggc aattcggctc aaggccggcg atactcactc gaccgattat accatgggtg   1560
aatgggctgc aaacaagaaa ggtggcatcc gtgcttaccc attctcaacc tccctgaaaa   1620
ccaaccctct cacctacacc agtctcaatg aattggacga agtgcatgcc atcggcgcgg   1680
tgtgggctaa cgtattgtac gagctgttgt ggaacttgat cgataagcac ggcaagaatg   1740
acgggccaaa gcccgagttc aaggatggag ttccgactga cggcaagtat ctcgccatga   1800
agctggtgat tgatggcata gcattgtaag tgccaacctc gtttcctctt tctacctatc   1860
gcaggggcta accttgactt ttaggcaacc ttgcaaccc aactgtgtcc aggctcgcga    1920
cgccatcctc gatgccgata aggctctcac cgatggtgct aacaagtgcg agatttggaa   1980
ggcgtttgct aagcgtggtt tgggtgaagg cgctgaatac catgcgtctc gtcgggtggg   2040
cagtgataag gtgccctctg atgcttgcta g                                  2071
```

<210> SEQ ID NO 28
<211> LENGTH: 1488
<212> TYPE: DNA
<213> ORGANISM: Aspergillus oryzae

<400> SEQUENCE: 28

-continued

```
atgagaggca tcctcggcct ttccctgctg ccactactag cagcggcctc ccccgttgct    60
gttgactcca tccacaacgg agcggctccc attctttcgg cctcaaatgc caaagaggtt   120
ccagactctt acattgtcgt cttcaagaag catgtttccg ctgaaacggc tgctgctcat   180
cacacctggg tgcaggacat ccacgattcg atgactggac gcatcgacct gaagaagcgc   240
tctctttttg gtttcagtga tgaccttttac ctcggtctca agaacacctt cgatatcgcc   300
gggtccctag cgggctactc cggacatttc catgaggatg tgatcgagca ggtccggaga   360
catcctgatg ttgaatacat cgagaaagac accgaagtcc acaccatgga ggagacaacc   420
gagaagaatg ctccctgggg cttggctcgt atctctcacc gtgacagcct ctcgttcggt   480
acctttaaca gtacctgta tgcttcggaa ggcggtgagg gtgtcgatgc ttatactatt   540
gacactggta tcaacattga gcatgtcgat ttcgaggatc gagcacactg gggaaagacc   600
atccctagca atgatgagga tgcggatggc aacggacacg gaactcactg ctccggaacc   660
attgctggta agaagtacgg tgttgccaag aaggccaaca tctatgccgt caaggtcttg   720
aggtccagcg ttctggcac tatgtccgat gtcgttctgg tgtcgagtg ggccgtccag   780
tcccacctca agaaggctaa ggacgccaaa gatgccaagg tcaagggttt caagggcagc   840
gttgccaaca tgagtcttgg tggtgccaag tccaggaccc ttgaggctgc tgtcaatgct   900
ggtgttgagg ctggtcttca cttcgccgtt gctgctggta acgacaatgc cgatgcctgc   960
aactactccc ctgctgccgc tgagaatgcc atcactgtcg gtgcctcgac ccttcaggat  1020
gagcgtgctt acttctccaa ctacggaaag tgcactgaca tctttgcccc gggtcccaac  1080
attctttcca cctggactgg cagcaagcac gctgtcaaca ccatctctgg aacctctatg  1140
gcttctcctc acattgctgg tctgctggcc tacttcgttt ctctgcagcc tgctcaggac  1200
tctgctttcg ctgtcgatga gcttactcct gccaagctca agaaggatat catctccatc  1260
gccacccagg gtgcccttac tgatatccca tctgacaccc caaccttct cgcctggaac  1320
ggcggtggtg ccgacaacta cacccagatt gtcgccaagg gtggatacaa ggccggcagt  1380
gacaaccta aggaccgctt tgacggacta gtcaacaagg ccgagaagtt gctcgctgag  1440
gagcttggag ctatttacag tgagatccag ggtgctgttg ttgcatag               1488
```

<210> SEQ ID NO 29
<211> LENGTH: 2511
<212> TYPE: DNA
<213> ORGANISM: Aspergillus oryzae

<400> SEQUENCE: 29

```
atgcggcttt ccgaaagtgc aacggtagcg ttcggccttt tttgtgccgc gacggcatca    60
gcccatcctc gacgctccta cgagacgcgc gatttctttg ctcttcatct tgacgattcc   120
acctccccag acgagatcgc ccaacgcctc ggagcacgcc acgagggtca agtaggtgaa   180
ctcacacaac accataccctt ctctataccc aaggagaacg gtgcagacct cgatgcgctg   240
ctcgaacatg cacgaatcag aaaaaggtca agtcgtgccg aaggacgtgg catgacgttg   300
gacaaggaaa gagatttgag tggtatactc tggtctcaaa agttagcccc aaaacagcga   360
ctagtaaaga gggctcctcc aacaaatgtg gcgtcgaggg ggtctgtgaa agaagaggac   420
cccgtagctg cccaagctca gaaacggatt gcctcttcac ttgggattac agatcccatt   480
ttcggcggac agtggcatct ttacaacact gtccaggttg ccatgatct caatgtttcg   540
gacgtctggt tagaaggtat caccgggaaa ggtgtcatca cggctgtggt cgatgacgga   600
```

```
ctggacatgt acagcaacga cctcaaaccg aactactttg ctgagggctc ctacgatttt      660
aacgaccatg taccggagcc cagaccgcgg cttggtgatg atagacacgg cacaagatgt      720
gctggtgaaa ttggagcagc taggaatgat gtctgtggag taggcgttgc atacgacagc      780
caagttgccg gaattcggat tttgtccgca cccattgacg acgcagatga ggctgctgcc      840
atcaactatg gctttcagcg caatgatata tattcatgct cttggggccc tccggatgat      900
ggcgccacga tggaggcgcc agggattctt atcaaacgag ctatggttaa cggtatccaa      960
aatggccgag gaggcaaagg ttctattttc gtctttgcag ctggaaatgg tgcagggtac     1020
gatgacaact gcaatttcga cggctacaca aacagcattt acagcatcac cgtcggcgct     1080
attgatcgag agggcaaaca tcccagctac tcggaatcat gctctgccca gttggttgtc     1140
gcttatagca gtggctcgag tgacgcgatt cataccactg acgttggaac tgataaatgt     1200
tattcacttc acggcggaac ttctgccgca ggcccgctag ctgcgggtac tattgcccct     1260
gctcttagtg cccgaccgga actaacttgg cgagatgccc agtacctgat gatagagacc     1320
gcagttcccg tccacgaaga cgacgggagc tggcagacta ccaaaatggg gaagaagttt     1380
agccatgact gggggtttgg gaaagtagat gcatattcac tggtacagct ggccaagacg     1440
tgggagctgg tgaaaccaca ggcgtggttc cactcaccgt ggctgcgggt gaagcatgaa     1500
atcccacaag gtgaccaggg tcttgccagc tcatacgaaa ttaccaagga tatgatgtat     1560
caggccaata tcgagaaact ggaacatgtc actgtgacca tgaatgtaaa tcacactcgc     1620
cgaggcgaca tcagtgtgga gttgcgcagc cccgaaggta tcgtcagtca tctgagtaca     1680
gcgcggcggt cagataatgc aaaggctggc tatgaagact ggacgtttat gactgtggct     1740
cattggggtg agtccggtgt tggaaagtgg acggtcattg tgaaggatac caatgtcaat     1800
gatcatgttg gagaattcat cgactggcgg ctcaacctct ggggactttc gatcgacggc     1860
tccagccagc cccttcatcc tatgcccgat gagcatgacg atgaccactc gattgaagat     1920
gccattgttg ttaccactag tgttgatcct ctcccaacta agactgaagc cccacctgtc     1980
ccaactgatc ccgtggatcg tcctgtgaac gcaaagccat ctgcgcagcc aacgacgcct     2040
tcagaggctc ctgctcaaga gacatctgaa gctcccaccc cgacgaaacc cagttctact     2100
gaatcacctt ctaccaccac ctctgcggat agctttttgc cgtccttctt ccccacgttc     2160
ggcgcttcaa aacggaccca ggcttggatt tacgctgcga tcagttcgat cattgtattc     2220
tgtattggcc ttggtgtcta cttccacgta cagcgacgaa agcgtctgcg taatgatccg     2280
cgtgatgact acgatttcga aatgatagaa gatgaggatg aaacgcaggc tatgaacggg     2340
cgttcgggtc gtacacaacg ccggggcggc gagctttaca atgctttcgc tggggagagc     2400
gacgaagaac ctttgtttag cgacgatgag gatgagcctt atagggatca tgcccttagt     2460
gaagatcggg aacggcgagg gagcacaagt ggtgaccatg ctcggtcata g             2511
```

<210> SEQ ID NO 30
<211> LENGTH: 403
<212> TYPE: PRT
<213> ORGANISM: Aspergillus oryzae

<400> SEQUENCE: 30

```
Met Gln Ser Ile Lys Arg Thr Leu Leu Leu Gly Ala Ile Leu Pro
1               5                   10                  15

Ala Val Leu Gly Ala Pro Val Gln Glu Thr Arg Arg Ala Ala Glu Lys
                20                  25                  30

Leu Pro Gly Lys Tyr Ile Val Thr Phe Lys Pro Gly Ile Asp Glu Ala
```

```
                35                  40                  45
Lys Ile Gln Glu His Thr Thr Trp Ala Thr Asn Ile His Gln Arg Ser
 50                  55                  60
Leu Glu Arg Arg Gly Ala Thr Gly Gly Asp Leu Pro Val Gly Ile Glu
 65                  70                  75                  80
Arg Asn Tyr Lys Ile Asn Lys Phe Ala Ala Tyr Ala Gly Ser Phe Asp
                 85                  90                  95
Asp Ala Thr Ile Glu Glu Ile Arg Lys Asn Glu Asp Val Ala Tyr Val
            100                 105                 110
Glu Glu Asp Gln Ile Tyr Tyr Leu Asp Gly Leu Thr Thr Gln Lys Ser
        115                 120                 125
Ala Pro Trp Gly Leu Gly Ser Ile Ser His Lys Gly Gln Gln Ser Thr
130                 135                 140
Asp Tyr Ile Tyr Asp Thr Ser Ala Gly Glu Gly Thr Tyr Ala Tyr Val
145                 150                 155                 160
Val Asp Ser Gly Val Asn Val Asp His Glu Glu Phe Glu Gly Arg Ala
                165                 170                 175
Ser Lys Ala Tyr Asn Ala Gly Gly Gln His Val Asp Ser Ile Gly
            180                 185                 190
His Gly Thr His Val Ser Gly Thr Ile Ala Gly Lys Thr Tyr Gly Ile
        195                 200                 205
Ala Lys Lys Ala Ser Ile Leu Ser Val Lys Val Phe Gln Gly Glu Ser
210                 215                 220
Ser Ser Thr Ser Val Ile Leu Asp Gly Phe Asn Trp Ala Ala Asn Asp
225                 230                 235                 240
Ile Val Ser Lys Lys Arg Thr Ser Lys Ala Ala Ile Asn Met Ser Leu
                245                 250                 255
Gly Gly Gly Tyr Ser Lys Ala Phe Asn Asp Ala Val Glu Asn Ala Phe
            260                 265                 270
Glu Gln Gly Val Leu Ser Val Ala Ala Gly Asn Glu Asn Ser Asp
        275                 280                 285
Ala Gly Gln Thr Ser Pro Ala Ser Ala Pro Asp Ala Ile Thr Val Ala
290                 295                 300
Ala Ile Gln Lys Ser Asn Asn Arg Ala Ser Phe Ser Asn Phe Gly Lys
305                 310                 315                 320
Val Val Asp Val Phe Ala Pro Gly Gln Asp Ile Leu Ser Ala Trp Ile
                325                 330                 335
Gly Ser Ser Ala Thr Asn Thr Ile Ser Gly Thr Ser Met Ala Thr
            340                 345                 350
Pro His Ile Val Gly Leu Ser Leu Tyr Leu Ala Ala Leu Glu Asn Leu
        355                 360                 365
Asp Gly Pro Ala Ala Val Thr Lys Arg Ile Lys Glu Leu Ala Thr Lys
370                 375                 380
Asp Val Val Lys Asp Val Lys Gly Ser Pro Asn Leu Leu Ala Tyr Asn
385                 390                 395                 400
Gly Asn Ala

<210> SEQ ID NO 31
<211> LENGTH: 634
<212> TYPE: PRT
<213> ORGANISM: Aspergillus oryzae

<400> SEQUENCE: 31

Met Arg Gly Leu Leu Leu Ala Gly Ala Leu Gly Leu Pro Leu Ala Val
```

-continued

```
1               5                   10                  15

Leu Ala His Pro Thr His His Ala His Gly Leu Gln Arg Arg Thr Val
                20                  25                  30

Asp Leu Asn Ser Phe Arg Leu His Gln Ala Ala Lys Tyr Ile Asn Ala
                35                  40                  45

Thr Glu Ser Ser Ser Asp Val Ser Ser Ser Phe Ser Pro Phe Thr Glu
                50                  55                  60

Gln Ser Tyr Val Glu Thr Ala Thr Gln Leu Val Lys Asn Ile Leu Pro
65                              70                  75              80

Asp Ala Thr Phe Arg Val Val Lys Asp His Tyr Ile Gly Ser Asn Gly
                        85                  90                  95

Val Ala His Val Asn Phe Arg Gln Thr Val His Gly Leu Asp Ile Asp
                100                 105                 110

Asn Ala Asp Phe Asn Val Asn Val Gly Lys Asn Gly Lys Ile Phe Ser
                115                 120                 125

Tyr Gly His Ser Phe Tyr Thr Gly Lys Ile Pro Asp Ala Asn Pro Leu
                130                 135                 140

Thr Lys Arg Asp Tyr Thr Asp Pro Val Ala Ala Leu Arg Gly Thr Asn
145                     150                 155                 160

Glu Ala Leu Gln Leu Ser Ile Thr Leu Asp Gln Val Ser Thr Glu Ala
                165                 170                 175

Thr Glu Asp Lys Glu Ser Phe Asn Phe Lys Gly Val Ser Gly Thr Val
                180                 185                 190

Ser Asp Pro Lys Ala Gln Leu Val Tyr Leu Val Lys Glu Asp Gly Ser
                195                 200                 205

Leu Ala Leu Thr Trp Lys Val Glu Thr Asp Ile Asp Ser Asn Trp Leu
210                     215                 220

Leu Thr Tyr Ile Asp Ala Asn Thr Gly Lys Asp Val His Gly Val Val
225                     230                 235                 240

Asp Tyr Val Ala Glu Ala Asp Tyr Gln Val Tyr Ala Trp Gly Ile Asn
                245                 250                 255

Asp Pro Thr Glu Gly Pro Arg Thr Val Ile Ser Asp Pro Trp Asp Ser
                260                 265                 270

Ser Ala Ser Ala Phe Thr Trp Ile Ser Asp Gly Glu Asn Asn Tyr Thr
                275                 280                 285

Thr Thr Arg Gly Asn Asn Gly Ile Ala Gln Ser Asn Pro Thr Gly Gly
                290                 295                 300

Ser Gln Tyr Leu Lys Asn Tyr Arg Pro Asp Ser Pro Asp Leu Lys Phe
305                     310                 315                 320

Gln Tyr Pro Tyr Ser Leu Asn Ala Thr Pro Pro Glu Ser Tyr Ile Asp
                325                 330                 335

Ala Ser Ile Thr Gln Leu Phe Tyr Thr Ala Asn Thr Tyr His Asp Leu
                340                 345                 350

Leu Tyr Thr Leu Gly Phe Asn Glu Glu Ala Gly Asn Phe Gln Tyr Asp
                355                 360                 365

Asn Asn Gly Lys Gly Gly Ala Gly Asn Asp Tyr Val Ile Leu Asn Ala
                370                 375                 380

Gln Asp Gly Ser Gly Thr Asn Asn Ala Asn Phe Ala Thr Pro Pro Asp
385                     390                 395                 400

Gly Gln Pro Gly Arg Met Arg Met Tyr Ile Trp Thr Glu Ser Gln Pro
                405                 410                 415

Tyr Arg Asp Gly Ser Phe Glu Ala Gly Ile Val Ile His Glu Tyr Thr
                420                 425                 430
```

His Gly Leu Ser Asn Arg Leu Thr Gly Gly Pro Ala Asn Ser Arg Cys
        435                 440                 445

Leu Asn Ala Leu Glu Ser Gly Gly Met Gly Glu Gly Trp Gly Asp Phe
        450                 455                 460

Met Ala Thr Ala Ile Arg Leu Lys Ala Gly Asp Thr His Ser Thr Asp
465                 470                 475                 480

Tyr Thr Met Gly Glu Trp Ala Ala Asn Lys Lys Gly Gly Ile Arg Ala
                485                 490                 495

Tyr Pro Phe Ser Thr Ser Leu Glu Thr Asn Pro Leu Thr Tyr Thr Ser
                500                 505                 510

Leu Asn Glu Leu Asp Glu Val His Ala Ile Gly Ala Val Trp Ala Asn
        515                 520                 525

Val Leu Tyr Glu Leu Leu Trp Asn Leu Ile Asp Lys His Gly Lys Asn
        530                 535                 540

Asp Gly Pro Lys Pro Glu Phe Lys Asp Gly Val Pro Thr Asp Gly Lys
545                 550                 555                 560

Tyr Leu Ala Met Lys Leu Val Ile Asp Gly Ile Ala Leu Gln Pro Cys
                565                 570                 575

Asn Pro Asn Cys Val Gln Ala Arg Asp Ala Ile Leu Asp Ala Asp Lys
                580                 585                 590

Ala Leu Thr Asp Gly Ala Asn Lys Cys Glu Ile Trp Lys Ala Phe Ala
        595                 600                 605

Lys Arg Gly Leu Gly Glu Gly Ala Glu Tyr His Ala Ser Arg Arg Val
        610                 615                 620

Gly Ser Asp Lys Val Pro Ser Asp Ala Cys
625                 630

<210> SEQ ID NO 32
<211> LENGTH: 495
<212> TYPE: PRT
<213> ORGANISM: Aspergillus oryzae

<400> SEQUENCE: 32

Met Arg Gly Ile Leu Gly Leu Ser Leu Leu Pro Leu Leu Ala Ala Ala
1               5                   10                  15

Ser Pro Val Ala Val Asp Ser Ile His Asn Gly Ala Ala Pro Ile Leu
                20                  25                  30

Ser Ala Ser Asn Ala Lys Glu Val Pro Asp Ser Tyr Ile Val Val Phe
        35                  40                  45

Lys Lys His Val Ser Ala Glu Thr Ala Ala Ala His His Thr Trp Val
    50                  55                  60

Gln Asp Ile His Asp Ser Met Thr Gly Arg Ile Asp Leu Lys Lys Arg
65                  70                  75                  80

Ser Leu Phe Gly Phe Ser Asp Asp Leu Tyr Leu Gly Leu Lys Asn Thr
                85                  90                  95

Phe Asp Ile Ala Gly Ser Leu Ala Gly Tyr Ser Gly His Phe His Glu
            100                 105                 110

Asp Val Ile Glu Gln Val Arg Arg His Pro Asp Val Glu Tyr Ile Glu
        115                 120                 125

Lys Asp Thr Glu Val His Thr Met Glu Glu Thr Thr Glu Lys Asn Ala
    130                 135                 140

Pro Trp Gly Leu Ala Arg Ile Ser His Arg Asp Ser Leu Ser Phe Gly
145                 150                 155                 160

Thr Phe Asn Lys Tyr Leu Tyr Ala Ser Glu Gly Gly Glu Gly Val Asp

```
                165                 170                 175
Ala Tyr Thr Ile Asp Thr Gly Ile Asn Ile Glu His Val Asp Phe Glu
            180                 185                 190

Asp Arg Ala His Trp Gly Lys Thr Ile Pro Ser Asn Asp Glu Asp Ala
        195                 200                 205

Asp Gly Asn Gly His Gly Thr His Cys Ser Gly Thr Ile Ala Gly Lys
    210                 215                 220

Lys Tyr Gly Val Ala Lys Ala Asn Ile Tyr Ala Val Lys Val Leu
225                 230                 235                 240

Arg Ser Ser Gly Ser Gly Thr Met Ser Asp Val Val Leu Gly Val Glu
                245                 250                 255

Trp Ala Val Gln Ser His Leu Lys Lys Ala Lys Asp Ala Lys Asp Ala
            260                 265                 270

Lys Val Lys Gly Phe Lys Gly Ser Val Ala Asn Met Ser Leu Gly Gly
        275                 280                 285

Ala Lys Ser Arg Thr Leu Glu Ala Ala Val Asn Ala Gly Val Glu Ala
    290                 295                 300

Gly Leu His Phe Ala Val Ala Ala Gly Asn Asp Asn Ala Asp Ala Cys
305                 310                 315                 320

Asn Tyr Ser Pro Ala Ala Ala Glu Asn Ala Ile Thr Val Gly Ala Ser
                325                 330                 335

Thr Leu Gln Asp Glu Arg Ala Tyr Phe Ser Asn Tyr Gly Lys Cys Thr
            340                 345                 350

Asp Ile Phe Ala Pro Gly Pro Asn Ile Leu Ser Thr Trp Thr Gly Ser
        355                 360                 365

Lys His Ala Val Asn Thr Ile Ser Gly Thr Ser Met Ala Ser Pro His
    370                 375                 380

Ile Ala Gly Leu Leu Ala Tyr Phe Val Ser Leu Gln Pro Ala Gln Asp
385                 390                 395                 400

Ser Ala Phe Ala Val Asp Glu Leu Thr Pro Ala Lys Leu Lys Lys Asp
                405                 410                 415

Ile Ile Ser Ile Ala Thr Gln Gly Ala Leu Thr Asp Ile Pro Ser Asp
            420                 425                 430

Thr Pro Asn Leu Leu Ala Trp Asn Gly Gly Gly Ala Asp Asn Tyr Thr
        435                 440                 445

Gln Ile Val Ala Lys Gly Gly Tyr Lys Ala Gly Ser Asp Asn Leu Lys
    450                 455                 460

Asp Arg Phe Asp Gly Leu Val Asn Lys Ala Glu Lys Leu Leu Ala Glu
465                 470                 475                 480

Glu Leu Gly Ala Ile Tyr Ser Glu Ile Gln Gly Ala Val Val Ala
                485                 490                 495

<210> SEQ ID NO 33
<211> LENGTH: 836
<212> TYPE: PRT
<213> ORGANISM: Aspergillus oryzae

<400> SEQUENCE: 33

Met Arg Leu Ser Glu Ser Ala Thr Val Ala Phe Gly Leu Phe Cys Ala
1               5                   10                  15

Ala Thr Ala Ser Ala His Pro Arg Arg Ser Tyr Glu Thr Arg Asp Phe
            20                  25                  30

Phe Ala Leu His Leu Asp Asp Ser Thr Ser Pro Asp Glu Ile Ala Gln
        35                  40                  45
```

-continued

```
Arg Leu Gly Ala Arg His Glu Gly Gln Val Gly Glu Leu Thr Gln His
 50                  55                  60

His Thr Phe Ser Ile Pro Lys Glu Asn Gly Ala Asp Leu Asp Ala Leu
 65                  70                  75                  80

Leu Glu His Ala Arg Ile Arg Lys Arg Ser Arg Ala Glu Gly Arg
                 85                  90                  95

Gly Met Thr Leu Asp Lys Glu Arg Asp Leu Ser Gly Ile Leu Trp Ser
                100                 105                 110

Gln Lys Leu Ala Pro Lys Gln Arg Leu Val Lys Arg Ala Pro Pro Thr
            115                 120                 125

Asn Val Ala Ser Arg Gly Ser Val Lys Glu Glu Asp Pro Val Ala Ala
130                 135                 140

Gln Ala Gln Lys Arg Ile Ala Ser Ser Leu Gly Ile Thr Asp Pro Ile
145                 150                 155                 160

Phe Gly Gly Gln Trp His Leu Tyr Asn Thr Val Gln Val Gly His Asp
                165                 170                 175

Leu Asn Val Ser Asp Val Trp Leu Glu Gly Ile Thr Gly Lys Gly Val
                180                 185                 190

Ile Thr Ala Val Val Asp Asp Gly Leu Asp Met Tyr Ser Asn Asp Leu
            195                 200                 205

Lys Pro Asn Tyr Phe Ala Glu Gly Ser Tyr Asp Phe Asn Asp His Val
210                 215                 220

Pro Glu Pro Arg Pro Arg Leu Gly Asp Asp Arg His Gly Thr Arg Cys
225                 230                 235                 240

Ala Gly Glu Ile Gly Ala Ala Arg Asn Asp Val Cys Gly Val Gly Val
                245                 250                 255

Ala Tyr Asp Ser Gln Val Ala Gly Ile Arg Ile Leu Ser Ala Pro Ile
            260                 265                 270

Asp Asp Ala Asp Glu Ala Ala Ile Asn Tyr Gly Phe Gln Arg Asn
                275                 280                 285

Asp Ile Tyr Ser Cys Ser Trp Gly Pro Pro Asp Asp Gly Ala Thr Met
            290                 295                 300

Glu Ala Pro Gly Ile Leu Ile Lys Arg Ala Met Val Asn Gly Ile Gln
305                 310                 315                 320

Asn Gly Arg Gly Gly Lys Gly Ser Ile Phe Val Phe Ala Ala Gly Asn
                325                 330                 335

Gly Ala Gly Tyr Asp Asp Asn Cys Asn Phe Asp Gly Tyr Thr Asn Ser
            340                 345                 350

Ile Tyr Ser Ile Thr Val Gly Ala Ile Asp Arg Glu Gly Lys His Pro
        355                 360                 365

Ser Tyr Ser Glu Ser Cys Ser Ala Gln Leu Val Val Ala Tyr Ser Ser
    370                 375                 380

Gly Ser Ser Asp Ala Ile His Thr Thr Asp Val Gly Thr Asp Lys Cys
385                 390                 395                 400

Tyr Ser Leu His Gly Thr Ser Ala Ala Gly Pro Leu Ala Ala Gly
                405                 410                 415

Thr Ile Ala Leu Ala Leu Ser Ala Arg Pro Glu Leu Thr Trp Arg Asp
            420                 425                 430

Ala Gln Tyr Leu Met Ile Glu Thr Ala Val Pro Val His Glu Asp Asp
                435                 440                 445

Gly Ser Trp Gln Thr Thr Lys Met Gly Lys Lys Phe Ser His Asp Trp
450                 455                 460

Gly Phe Gly Lys Val Asp Ala Tyr Ser Leu Val Gln Leu Ala Lys Thr
```

```
            465                 470                 475                 480
Trp Glu Leu Val Lys Pro Gln Ala Trp Phe His Ser Pro Trp Leu Arg
                485                 490                 495

Val Lys His Glu Ile Pro Gln Gly Asp Gln Gly Leu Ala Ser Ser Tyr
                500                 505                 510

Glu Ile Thr Lys Asp Met Met Tyr Gln Ala Asn Ile Glu Lys Leu Glu
                515                 520                 525

His Val Thr Val Thr Met Asn Val Asn His Thr Arg Arg Gly Asp Ile
                530                 535                 540

Ser Val Glu Leu Arg Ser Pro Glu Gly Ile Val Ser His Leu Ser Thr
545                 550                 555                 560

Ala Arg Arg Ser Asp Asn Ala Lys Ala Gly Tyr Glu Asp Trp Thr Phe
                565                 570                 575

Met Thr Val Ala His Trp Gly Glu Ser Gly Val Gly Lys Trp Thr Val
                580                 585                 590

Ile Val Lys Asp Thr Asn Val Asn Asp His Val Gly Glu Phe Ile Asp
                595                 600                 605

Trp Arg Leu Asn Leu Trp Gly Leu Ser Ile Asp Gly Ser Ser Gln Pro
                610                 615                 620

Leu His Pro Met Pro Asp Glu His Asp Asp His Ser Ile Glu Asp
625                 630                 635                 640

Ala Ile Val Val Thr Thr Ser Val Asp Pro Leu Pro Thr Lys Thr Glu
                645                 650                 655

Ala Pro Pro Val Pro Thr Asp Pro Val Asp Arg Pro Val Asn Ala Lys
                660                 665                 670

Pro Ser Ala Gln Pro Thr Thr Pro Ser Glu Ala Pro Ala Gln Glu Thr
                675                 680                 685

Ser Glu Ala Pro Thr Pro Thr Lys Pro Ser Ser Thr Glu Ser Pro Ser
                690                 695                 700

Thr Thr Thr Ser Ala Asp Ser Phe Leu Pro Ser Phe Pro Thr Phe
705                 710                 715                 720

Gly Ala Ser Lys Arg Thr Gln Ala Trp Ile Tyr Ala Ala Ile Ser Ser
                725                 730                 735

Ile Ile Val Phe Cys Ile Gly Leu Gly Val Tyr Phe His Val Gln Arg
                740                 745                 750

Arg Lys Arg Leu Arg Asn Asp Pro Arg Asp Asp Tyr Asp Phe Glu Met
                755                 760                 765

Ile Glu Asp Glu Asp Glu Thr Gln Ala Met Asn Gly Arg Ser Gly Arg
                770                 775                 780

Thr Gln Arg Arg Gly Gly Glu Leu Tyr Asn Ala Phe Ala Gly Glu Ser
785                 790                 795                 800

Asp Glu Glu Pro Leu Phe Ser Asp Asp Glu Asp Glu Pro Tyr Arg Asp
                805                 810                 815

His Ala Leu Ser Glu Asp Arg Glu Arg Gly Ser Thr Ser Gly Asp
                820                 825                 830

His Ala Arg Ser
                835
```

US 7,858,360 B2

USE OF FUNGAL MUTANTS FOR EXPRESSION OF ANTIBODIES

CROSS-REFERENCE TO RELATED APPLICATIONS

This application is a 35 U.S.C. 371 national application of PCT/DK2006/000586 filed Oct. 17, 2006, which claims priority or the benefit under 35 U.S.C. 119 of Danish application no. PA 2005 01452 filed Oct. 17, 2005 and U.S. provisional application No. 60/728,953 filed Oct. 20, 2005, the contents of which are fully incorporated herein by reference.

FIELD OF THE INVENTION

The present invention relates to a filamentous fungal cell in which an endogenous alkaline protease, an endogenous metalloprotease and an endogenous serine protease activity have been completely or partially inactivated. Furthermore the present invention relates to a method for producing a heterologous polypeptide in a filamentous fungal host cell.

BACKGROUND OF THE INVENTION

The use of recombinant host cells in the expression of heterologous proteins has in recent years greatly simplified the production of large quantities of commercially valuable proteins which otherwise are obtainable only by purification from their native sources. Currently, there is a varied selection of expression systems from which to choose for the production of any given protein, including bacterial and eukaryotic hosts. The selection of an appropriate expression system often depends not only on the ability of the host cell to produce adequate yields of the protein in an active state, but, to a large extent, may also be governed by the intended end use of the protein.

One problem frequently encountered is the high level of proteolytic enzymes produced by a given host cell or present in the culture medium. Proteases are a major problem for the production of heterologous proteins in filamentous fungi, since they are present at every stage of the secretion process as well as several extracellular proteases.

It has been suggested that one could provide host organisms deprived of the ability to produce specific proteolytic compounds. For example, International Patent Application WO 90/00192 (Genencor) describes filamentous fungal hosts incapable of secreting enzymatically active aspartic proteinase, and EP 574 347 (Ciba Geigy AG) describes *Aspergillus* hosts defective in a serine protease of the subtilisin-type.

Other examples of proteases which have been reported to reduce the stability of protein products include metalloproteases and alkaline proteases.

WO 1998/012300 describes fungal hosts having improved stability of heterologous protein products in which the host cell have been genetically modified to express significantly reduced levels of both a metalloprotease and an alkaline protease.

Another intracellular protease, a serine protease of the subtilisin type produced e.g. by *A. niger* and designated PepC has been described, the gene expressing it cloned, and a deletion mutant described in EP 574 347 and in Frederick et al., *Gene*, 125 57-64 (1993).

Another group of processing proteases is the kexin family of proteases, which recognizes dibasic amino acid motifs and are involved in removing N-terminal propeptides. Kexin proteases have a narrow substrate specificity. Fungal kexin like maturases have been cloned and characterized in *Aspergillus niger* (Jalving et al., 2000, Applied and Environmental Microbiology 66:363-368), in *Aspergillus nidulans*, designated KpcA (Kwon et al., 2001, Molecular Cell 12:142-147), and in *Aspergillus oryzae* (Mizutani et al., 2004, Eukaryotic Cell 3:1036-1048).

For heterologous production of recombinant proteins in a fungal host the choice of a suitable host resulting in the optimal expression and stability of the recombinant protein is to a large extent dependent on the protein and thus the presence of specific protease recognition sites in the protein. The presence of such recognition sites can be very difficult to predict. It is therefore desirable to identify new mutant fungal strains specifically tailored to the production of a desired protein. The present invention relates to the identification of desired protease mutations in fungal host strains useful for the production of heterologous proteins and particularly to the combination of such mutations.

SUMMARY OF THE INVENTION

The present invention provides such useful protease deficient strains in which the expression of at least three proteases has been completely or partially abolished. The affected genes according to the invention encode an endogenous alkaline protease activity, an endogenous neutral metalloprotease activity and an endogenous serine protease activity of the subtilisin type. Optionally an endogenous calcium dependent, neutral, serine protease of the kexin subfamily has been completely or partially inactivated.

In a first aspect the present invention relates to a filamentous fungal cell in which an endogenous alkaline protease activity, an endogenous neutral metalloprotease activity and an endogenous serine protease activity of the subtilisin type have been completely or partially inactivated, wherein the alkaline protease, the neutral metalloprotease, and the serine protease of the subtilisin type are encoded from nucleotide sequences selected from the group consisting of:

(a) a nucleotide sequence encoding an alkaline protease having an amino acid sequence which has at least 65% identity with the amino acids of SEQ ID NO: 30, a nucleotide sequence encoding a neutral metalloprotease which has at least 65% identity with the amino acids of SEQ ID NO: 31, and a nucleotide sequence encoding a serine protease of the subtilisin type having an amino acid sequence which has at least 65% identity with the amino acids of SEQ ID NO: 32; or (b) a nucleotide sequence having at least 65% identity with SEQ ID NO: 26, a nucleotide sequence having at least 65% identity with SEQ ID NO: 27, and a nucleotide sequence having at least 65% identity with SEQ ID NO: 28; or (c) nucleotide sequences which hybridizes under at least medium stringency conditions with either of the nucleic acid sequences SEQ ID NO: 26, 27, or 28.

In a second aspect the present invention relates to a method for producing a heterologous polypeptide in a filamentous fungal host cell according to the invention, comprising:

(a) introducing into the host cell a nucleic acid sequence encoding the heterologous polypeptide;
(b) cultivating the cell from (a) in a suitable growth medium under conditions conducive for expression of the heterologous polypeptide; and
(c) isolating the protein product.

DETAILED DESCRIPTION OF THE INVENTION

The present invention relates to the expression of heterologous proteins in a filamentous fungal host, which has been modified compared to the parent fungal host in order to reduce the expression of endogenous proteases that would otherwise affect the production yield and stability of the heterologous protein.

In particular the filamentous fungal host cell has been modified in order to reduce or preferably abolish the expression of an endogenous alkaline protease, an endogenous metalloprotease, and an endogenous serine protease of the subtilisin type.

Metalloproteases

In the context of this invention, a metalloprotease is a proteolytic enzyme containing a catalytic zinc metal center which participates in the hydrolysis of the peptide backbone of the substrate. The active zinc centre differentiates these proteases from the calpains, whose activities are dependent upon the presence of calcium. Confirmation of a protease as a metalloprotease is by the reversible loss of proteolytic activity upon removal of the zinc centre with 1 mM 1,10-phenanthroline, and its restoration after titration with $Zn^{2+}$ (0.1-100 mM).

In particular, the metalloprotease contemplated in the context of this invention is a neutral metalloprotease, which is a metalloprotease possessing optimal proteolytic activity in the neutral pH region, i.e. in the range of about pH 6-8, preferably in the range of about pH 6.5-7.5, more specifically, around pH 7. More particularly, the metalloprotease contemplated in the context of this invention is a neutral *Aspergillus* metalloprotease of the group NpI or NpII (Tatsumi, et al., 1991, supra).

In a more particular embodiment, the metalloprotease is an *Aspergillus oryzae* neutral metalloprotease I (NpI) preferably encoded by a cDNA sequence comprising the nucleotide sequence presented as SEQ ID NO: 27 or a sequence homologous thereto. Particularly the homologous sequence has a degree of identity to SEQ ID NO: 27 of at least 60%, preferably at least 65%, more preferably at least 70%, more preferably at least 75%, more preferably at least 80%, more preferably at least 85%, even more preferably at least 90%, most preferably at least 95%, and even most preferably at least 97%.

Preferably the homologous sequence encodes a protease having an amino acid sequence which has a degree of identity to the amino acids of SEQ ID NO: 31 (i.e., the complete polypeptide including signal peptide and propeptide) of at least 60%, preferably at least 65%, more preferably at least 70%, more preferably at least 75%, more preferably at least 80%, more preferably at least 85%, even more preferably at least 90%, most preferably at least 95%, and even most preferably at least 97%, which have metalloprotease activity (hereinafter "homologous polypeptides").

Alkaline Proteases

In the context of this invention an alkaline protease is a serine protease with activity which peaks in the neutral to alkaline pH range. Analyses of the amino acid sequence of alkaline proteases indicate homology to the subtilase subgroup of subtilisin-like serine proteases. As summarised by Siezen, et al. (1991. Protein Eng. 4:719-737) more than 50 subtilases have been identified from a wide variety of organisms, ranging from various species of bacteria, including gram positive and gram negative species, to fungi and yeast to higher eukaryotes, including worms, insects, plants and mammals. The amino acid sequences have been determined in more than 40 of these subtilases, and reveal that the mature region of the enzyme ranges from 268 to 1775 amino acids in length and a pre-pro-region of 27 to 280 amino acids in the N-terminal vicinity. In fungi and yeast, the variation is apparently smaller, with corresponding ranges of 279 to 397 and 105 to 121 in fungi, and 297 to 677 and 126 to 280 in yeast. A cDNA fragment of the entire coding region of the alkaline protease from *Aspergillus oryzae* was cloned and expressed in *Saccharomyces cerevisiae* (Tatsumi, H, et al. 1989. Mol. Gen. Genet. 219:33-38). The primary structure was shown to share 29% to 44% homology with other sequenced subtilisins, and the three residues in the active site, Asp32, H is 64 and Ser221 in subtilisin BPN', were conserved.

In a particular embodiment, the alkaline protease is an *Aspergillus oryzae* alkaline protease (alp), preferably encoded by a cDNA sequence comprising the nucleotide sequence presented as SEQ ID NO: 26 or a sequence homologous thereto. Particularly the homologous sequence has a degree of identity to SEQ ID NO: 26 of at least 60%, preferably at least 65%, more preferably at least 70%, more preferably at least 75%, more preferably at least 80%, more preferably at least 85%, even more preferably at least 90%, most preferably at least 95%, and even most preferably at least 97%.

Preferably the homologous sequence encodes a protease having an amino acid sequence which has a degree of identity to the amino acids of SEQ ID NO: 30 (i.e., the complete polypeptide including signal peptide and propeptide) of at least 60%, preferably at least 65%, more preferably at least 70%, more preferably at least 75%, more preferably at least 80%, more preferably at least 85%, even more preferably at least 90%, most preferably at least 95%, and even most preferably at least 97%, which have alkaline protease activity (hereinafter "homologous polypeptides").

Serine Protease

In the context of this invention the protease is a serine protease with a broad range of activity between pH 4.5 and 11 which are released from a cell wall fraction. Analyses of the amino acid sequence of the serine proteases indicate homology to the subtilase subgroup of subtilisin-like serine proteases. As summarised by Siezen, et al. (1991. Protein Eng. 4:719-737) more than 50 subtilases have been identified from a wide variety of organisms, ranging from various species of bacteria, including gram positive and gram negative species, to fungi and yeast to higher eukaryotes, including worms, insects, plants and mammals. The amino acid sequences have been determined in more than 40 of these subtilases, and reveal that the mature region of the enzyme ranges from 268 to 1775 amino acids in length and a pre-pro-region of 27 to 280 amino acids in the N-terminal vicinity. In fungi and yeast, the variation is apparently smaller, with corresponding ranges of 279 to 397 and 105 to 121 in fungi, and 297 to 677 and 126 to 280 in yeast. Genomic clones of the entire coding region of the serine protease from *Aspergillus oryzae, Aspergillus fumigatus* and *Aspergillus niger* has been cloned (WO97/22705, Reichard et al. 2000. Int. J. Med. Microbiol. 290, 549-558, and Frederick et al 1993. Gene 125. 57-64.). The primary structure was shown to share 29% to 78% homology with other sequenced subtilisins, and the three residues in the active site, Asp32, H is 64 and Ser221 in subtilisin BPN', were conserved.

In a particular embodiment, the serine protease of the subtilisin type is an *Aspergillus oryzae* serine protease (pepC), preferably encoded by a cDNA sequence comprising the nucleotide sequence presented as SEQ. ID. NO: 28 or a sequence homologous thereto. Particularly the homologous sequence has a degree of identity to SEQ ID NO: 28 of at least 60%, preferably at least 65%, more preferably at least 70%, more preferably at least 75%, more preferably at least 80%, more preferably at least 85%, even more preferably at least 90%, most preferably at least 95%, and even most preferably at least 97%.

Preferably the homologous sequence encodes a protease having an amino acid sequence which has a degree of identity to the amino acids of SEQ ID NO: 32 (i.e., the complete polypeptide including signal peptide and propeptide) of at least 60%, preferably at least 65%, more preferably at least 70%, more preferably at least 75%, more preferably at least 80%, more preferably at least 85%, even more preferably at least 90%, most preferably at least 95%, and even most preferably at least 97%, which have serine protease activity (hereinafter "homologous polypeptides").

In a particular embodiment the filamentous fungal host cell in addition to the above endogenous proteases also has reduced or abolished expression of a serine protease of the kexin subfamily.

Serine Protease of the Kexin Subfamily

Kexin is a $Ca^{2+}$-dependent transmembrane serine protease that cleaves the secretory proproteins on the carboxyl side of Lys-Arg and Arg-Arg in a late Golgi compartment (Fuller and Thorner, 1989, PNAS 86:1434-1438; Mizuno et al., 1988, Biochem. Biophys. Res. Commun. 156:246-254). All members of the kexin subfamily are calcium-dependent, neutral serine proteases that are activated by the removal of the amino-terminal propeptide at a kexin-specific (auto) processing site. The active proteases all contain two additional domains, a subtilisin-like domain containing the catalytic triad and a conserved P or Homo B domain of approximately 150 residues. The P domain, which is absent in other subtilases, is essential for the catalytic activity and the stability of the protein. *Aspergillus* kexins are found in *Aspergillus nidulans* (Kwon et al., 2001, Mol. Cell. 12:142-147), *A. niger* (Jalving et al., 2000, Appl. Environ. Microbiol. 66:363-368), and *A. oryzae* (Mizutani et al., 2004, Eukaryotic Cell 3:1036-1048).

In a particular embodiment, the serine protease of the kexin subfamily is an *Aspergillus oryzae* serine protease (kexB), preferably encoded by a cDNA sequence comprising the nucleotide sequence presented as SEQ ID NO: 29 or a sequence homologous thereto. Particularly the homologous sequence has a degree of identity to SEQ ID NO: 29 of at least 60%, preferably at least 65%, more preferably at least 70%, more preferably at least 75%, more preferably at least 80%, more preferably at least 85%, even more preferably at least 90%, most preferably at least 95%, and even most preferably at least 97%.

Preferably the homologous sequence encodes a protease having an amino acid sequence which has a degree of identity to the amino acids of SEQ ID NO: 33 (i.e., the complete polypeptide including signal peptide and propeptide) of at least 60%, preferably at least 65%, more preferably at least 70%, more preferably at least 75%, more preferably at least 80%, more preferably at least 85%, even more preferably at least 90%, most preferably at least 95%, and even most preferably at least 97%, which have serine protease activity (hereinafter "homologous polypeptides").

In a particular embodiment the filamentous fungal cell according to the invention has the phenotype alp⁻, np1⁻, pepC⁻, and kexB⁻, wherein the alp gene is encoded by a nucleotide sequence which has at least 70% identity to SEQ ID NO: 26, the np1 gene is encoded by a nucleotide sequence which has at least 70% identity to SEQ ID NO: 27, the pepC gene is encoded by a nucleotide sequence which has at least 70% identity to SEQ ID NO: 28, and the kexB gene is encoded by a nucleotide sequence which has at least 70% identity to SEQ ID NO: 29.

In the above the nucleotide sequences referred to are the cDNA sequences (CDS without introns) corresponding to the mature mRNA after splicing.

Hybridization

For purposes of the present invention, hybridization indicates that the nucleic acid sequence hybridizes to at least one of the nucleic acid sequences shown in SEQ ID NO: 26, 27, 28, or 29 under very low to very high stringency conditions. Molecules to which the nucleotide sequence hybridizes under these conditions may be detected using X-ray film or by any other method known in the art. Whenever the term "polynucleotide probe" is used in the present context, it is to be understood that such a probe contains at least 15 nucleotides.

In one embodiment, the polynucleotide probe is the nucleotide sequence shown in SEQ ID NO: 26, 27, 28, or 29 or the complementary strand of SEQ ID NO: 26, 27, 28, or 29.

In one embodiment hybridization is performed under at least medium stringency conditions, more particularly under at least medium high stringency conditions, and even more particularly under at least high stringency conditions.

For long probes of at least 100 nucleotides in length, very low to very high stringency conditions are defined as prehybridization and hybridization at 42° C. in 5×SSPE, 1.0% SDS, 5×Denhardt's solution, 100 μg/ml sheared and denatured salmon sperm DNA, following standard Southern blotting procedures. Preferably, the long probes of at least 100 nucleotides do not contain more than 1000 nucleotides. For long probes of at least 100 nucleotides in length, the carrier material is finally washed three times each for 15 minutes using 2×SSC, 0.1% SDS at 42° C. (very low stringency), preferably washed three times each for 15 minutes using 0.5×SSC, 0.1% SDS at 42° C. (low stringency), more preferably washed three times each for 15 minutes using 0.2×SSC, 0.1% SDS at 42° C. (medium stringency), even more preferably washed three times each for 15 minutes using 0.2×SSC, 0.1% SDS at 55° C. (medium-high stringency), most preferably washed three times each for 15 minutes using 0.1×SSC, 0.1% SDS at 60° C. (high stringency), in particular washed three times each for 15 minutes using 0.1×SSC, 0.1% SDS at 68° C. (very high stringency).

Although not particularly preferred, it is contemplated that shorter probes, e.g. probes which are from about 15 to 99 nucleotides in length, such as from about 15 to about 70 nucleotides in length, may be also be used. For such short probes, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to 99 nucleotides in length, the carrier material is washed once in 6×SCC plus 0.1% SDS for 15 minutes and twice each for 15 minutes using 6×SSC at 5° C. to 10° C. below the calculated $T_m$.

Genetic Modifications of the Host Cell

The host cell of the invention, in order to express significantly reduced levels of metalloprotease, alkaline protease, and serine protease activity, and optionally serine protease of the kexin subfamily is genetically modified which may be achieved by using standard recombinant DNA technology known to the person skilled in the art. The gene sequences respectively responsible for production of the protease activity may be inactivated or partially or entirely eliminated. Thus, a host cell of the invention expresses reduced or undetectable levels of metalloprotease, alkaline protease, and serine protease or expresses functionally inactive proteases.

In a particular embodiment, the said inactivation is obtained by modification of the respective structural or regulatory regions encoded within the protease genes of interest. Known and useful techniques include, but are not limited to, specific or random mutagenesis, PCR generated mutagenesis, site specific DNA deletion, insertion and/or substitution, gene disruption or gene replacement, anti-sense techniques, or a combination thereof.

Mutagenesis may be performed using a suitable physical or chemical mutagenising agent. Examples of a physical or chemical mutagenising agent suitable for the present purpose include, but are not limited to, ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulfite, formic acid, and nucleotide analogues. When such agents are used, the mutagenesis is typically performed by incubating the cell to be mutagenised in the presence of the mutagenising agent of choice under suitable conditions, and selecting for cells showing a significantly reduced production of the protease of choice.

Measurements of the extracellular proteases activity of the alkaline and neutral metalloprotease I can be done as described by Markaryan et al (1996) J Bacteriology 178, no 8, 2211-2215. In short the strain is grown in a media which induce the production of extracellular proteases. The broth is then separate from the mycelium and are assay for alkaline and metalloproteinase activity with the substrate Suc-Ala-Ala-Pro-Leu-pNa and Abz-Ala-Ala-Phe-Phe-pNa, respectively.

Measurement of the intracellular Kexin is done as described by Jalving et al (2000) Applied and Environmental Microbiology 66, no 1, 363-368. In short strains are grown minimal media (COVE (1966) Biochim. Biophys. Acta 113, 51-56), mycelium is harvested, grounded and the membrane protein fraction were suspended in HEPES buffer and stored at −20° C. until used. The isolated membrane protein fraction were analysed for kexin activity by using the substrate Boc-Leu-Lys-Arg-MCA.

Measurement of pepC which are cell wall bound was done according to Reihard et al. (2000) Int. J. Med. Microbiol. 290, 85-96. In short strains are grown in minimal media (COVE (1966) Biochim. Biophys. Acta 113, 51-56), mycelium is harvested, grounded, and cell wall fragments were suspended in Na-citrate buffer and stored at −20° C. until used for proteinase assays. The isolated cell wall were analyse for pepC activity by an azocasein assay (Scharmann and Balke (1974) Physiol. Chem. 355, 443-450.

Modification may also be accomplished by the introduction, substitution or removal of one or more nucleotides in the structural sequence or a regulatory element required for the transcription or translation of the structural sequence. For example, nucleotides may be inserted or removed so as to result in the introduction of a stop codon, the removal of the start codon or a change of the open reading frame of the structural sequence. The modification or inactivation of the structural sequence or a regulatory element thereof may be accomplished by site-directed mutagenesis or PCR generated mutagenesis in accordance with methods known in the art. Although, in principle, the modification may be performed in vivo, i.e. directly on the cell expressing the metalloprotease, alkaline protease, and serine protease genes, it is presently preferred that the modification be performed in vitro as exemplified below.

A convenient way to inactivate or reduce the said protease production in a host cell of choice is based on techniques of gene interruption. In this method a DNA sequence corresponding to the endogenous gene or gene fragment of interest is mutagenised in vitro. Said DNA sequence thus encodes a defective gene which is then transformed into the host cell. By homologous recombination, the defective gene replaces the endogenous gene or gene fragment. It may be desirable that the defective gene or gene fragment also encodes a marker which may be used to select for transformants in which the respective genes encoding metalloprotease and/or alkaline protease have been modified or destroyed.

Methods for deleting or disrupting a targeted gene are specifically described by Miller, et al (1985. Mol. Cell. Biol. 5:1714-1721); WO 90/00192; May, G. (1992. *Applied Molecular Genetics of Filamentous Fungi*. J. R. Kinghorn and G. Turner, eds., Blackie Academic and Professional, pp. 1-25); and Turner, G. (1994. *Vectors for Genetic Manipulation*. S. D. Martinelli and J. R. Kinghorn, eds., Elsevier, pp. 641-665).

Alternatively, the modification or inactivation of the DNA sequence may be performed by established anti-sense techniques using a nucleotide sequence complementary to a coding sequence for a metalloprotease, e.g. the nucleotide sequences presented as SEQ ID NO: 27, an alkaline protease encoding sequence, e.g. the nucleotide sequence shown in SEQ. ID. NO: 26, or a serine protease of the subtilisin type and optionally also of the kexin subfamily, e.g. the nucleotide sequences shown in SEQ ID NO: 28 and SEQ ID NO: 29. The anti-sense technology and its application are described in detail in U.S. Pat. No. 5,190,931 (University of New York).

Therefore, due to genetic modification, the host cell of the invention expresses significantly reduced levels of metalloprotease, alkaline protease, and serine protease of the subtilisin type activity. In a particular embodiment the host cell in addition expresses significantly reduced levels of a serine protease of the kexin subfamily. In a particular embodiment, the level of these proteolytic activities expressed by the host cell is individually reduced more than about 50%, preferably more than about 85%, more preferably more than about 90%, and most preferably more than about 95%. In another particular embodiment, these proteolytic activities in the host cell of the invention may be reduced in any combination. In a most particular embodiment, the product expressed by the host cell is essentially free from proteolytic activity due to any of the above proteases.

Methods of Producing Proteins

By the method of the invention, the proteolytic activities of metalloprotease, alkaline protease, serine protease of the subtilisin type and optionally serine protease of the kexin subfamily are significantly reduced, thereby improving the stability and increasing the yield of susceptible protein products synthesised by the host cell of the invention. More specifically, by the method of the invention, the host cell is genetically modified within structural and/or regulatory regions encoding or controlling the metalloprotease, alkaline, serine protease of the subtilisin type and optionally serine protease of the kexin subfamily protease genes.

Therefore, another aspect of the invention provides a method of producing proteins in a host cell of the invention, including heterologous polypeptides, in which the method comprises introducing into said host cell a nucleic acid sequence encoding the protein product of interest, cultivating the host cell in a suitable growth medium, followed by recovery of the protein product.

Thus, the host cell of the invention must contain structural and regulatory genetic regions necessary for the expression of the desired product. The nature of such structural and regulatory regions greatly depends on the product and the host cell in question. The genetic design of the host cell of the invention may be accomplished by the person skilled in the art using standard recombinant DNA technology for the transformation or transfection of a host cell (vide, e.g., Sambrook et al., inter alia).

Preferably, the host cell is modified by methods known in the art for the introduction of an appropriate cloning vehicle, i.e. a plasmid or a vector, comprising a DNA fragment encoding the desired protein product. The cloning vehicle may be introduced into the host cell either as an autonomously replicating plasmid or integrated into the chromosome. Preferably, the cloning vehicle comprises one or more structural regions operably linked to one or more appropriate regulatory regions.

The structural regions are regions of nucleotide sequences encoding the desired protein product. The regulatory regions include promoter regions comprising transcription and translation control sequences, terminator regions comprising stop signals, and polyadenylation regions. The promoter, i.e. a nucleotide sequence exhibiting a transcriptional activity in the host cell of choice, may be one derived from a gene encoding an extracellular or an intracellular protein, preferably an enzyme, such as an amylase, a glucoamylase, a protease, a lipase, a cellulase, a xylanase, an oxidoreductase, a pectinase, a cutinase, or a glycolytic enzyme.

Examples of suitable promoters for heterologous protein expression in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

The cloning vehicle may also include a selectable marker, such as a gene product which complements a defect in the host cell, or one which confers antibiotic resistance. Examples of antibiotics useful as *Aspergillus* selection markers include hygromycin, phleomycin and basta. Other examples of *Aspergillus* selection markers include amdS, which encodes an enzyme involved in acetamide utilisation; pyrG, which encodes an enzyme involved in uridine biosynthesis; argB, which encodes an enzyme involved in arginine biosynthesis; niaD, which encodes an enzyme involved in the nitrate assimilation pathway; and sC, which encodes an enzyme involved in the sulfate assimilation pathway. Preferred for use in an *Aspergillus* host cell are the amdS and pyrG markers of *Aspergillus nidulans* or *Aspergillus oryzae*. Furthermore, selection may be accomplished by co-transformation, wherein the transformation is carried out with a mixture of two vectors and the selection is made for one vector only.

The procedures used to ligate the DNA construct of the invention, the promoter, terminator and other elements, respectively, and to insert them into suitable cloning vehicles containing the information necessary for replication, are well known to persons skilled in the art (vide e.g., Sambrook et al., 1989; inter alia).

The culture broth or medium used may be any conventional medium suitable for culturing the host cell of the invention, and formulated according to the principles of the prior art. The medium preferably contains carbon and nitrogen sources as well as other inorganic salts. Suitable media, e.g. minimal or complex media, are available from commercial suppliers, or may be prepared according to published recipes, as in *The Catalogue of Strains*, published by The American Type Culture Collection. Rockville Md., USA. 1970.

The appropriate pH for fermentation will often be dependent on such factors as the nature of the host cell to be used, the composition of the growth medium, the stability of the polypeptide of interest, and the like. Consequently, although the host cell of the invention may be cultured using any fermentation process performed at any pH, it is advantageous that the pH of the fermentation process is such that acidic and/or neutral protease activities of the host cell are essentially eliminated or at least significantly reduced. Thus, removal of aspartic protease activity as described in WO 90/00192 may also be accomplished by raising the fermentation pH, and does not present any additional advantageous effect on the yield of a desired protein from host cells cultivated in the alkaline pH range.

If the pH of the fermentation process is within the range from 5 to 11, such as from 6 to 10.5, 7 to 10, or 8 to 9.5, the activity of acidic proteases, such as aspartic and serine proteases, and neutral proteases in the pH ranges above 7, will be reduced or blocked. Examples of enzymes produced under alkaline fermentation conditions include endoglucanases, phytases and protein disulfide isomerases.

However, the alkaline pH range will support alkaline protease activity in an unmodified host cell, which, in turn, may potentially result in degradation of the polypeptide product of interest. Consequently, in such cases the inactivation of the gene encoding alkaline protease is especially advantageous.

Inactivation of the alkaline protease gene of the invention is also especially advantageous for certain host cells, as the levels of acidic, neutral and alkaline protease activities vary from species to species. For example, the level of alkaline protease activity in the *Aspergillus oryzae* is higher than in *Aspergillus niger*.

After cultivation, the desired protein is recovered by conventional methods of protein isolation and purification from a culture broth. Well established purification procedures include separating the cells from the medium by centrifugation or filtration, precipitating proteinaceous components of the medium by means of a salt such as ammonium sulphate, and chromatographic methods such as ion exchange chromatography, gel filtration chromatography, affinity chromatography, and the like.

Products

The desired end product, i.e. the heterologous protein, expressed by the host cell of the invention, may be any eubacterial or eukaryotic protein or peptide.

As defined herein, a "heterologous protein" is a protein or polypeptide gene product which is not native to the host cell, or is a native protein in which modifications have been made to alter the native sequence, or is a native protein whose expression is quantitatively altered as a result of a manipulation of a native regulatory sequence required for the expression of the native protein, such as a promoter, a ribosome binding site, etc., or other manipulation of the host cell by recombinant DNA techniques.

Sequence Identity and Alignment

In the present context, the homology between two amino acid sequences or between two nucleic acid sequences is described by the parameter "identity".

For purposes of the present invention, alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 183:63-98).

Multiple alignments of protein sequences may be made using "ClustalW" (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680). Multiple alignments of DNA sequences may be done using the protein alignment as a template, replacing the amino acids with the corresponding codon from the DNA sequence.

Alternatively different software can be used for aligning amino acid sequences and DNA sequences. The alignment of two amino acid sequences is e.g. determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"); e.g. SEQ ID NO: 32 and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap (in the alignment example below this is represented by "|"). The length of a sequence is the number of amino acid residues in the sequence (e.g. the length of SEQ ID NO: 32 is 495).

In the purely hypothetical alignment example below, the overlap is the amino acid sequence "HTWGER-NL" of Sequence 1; or the amino acid sequence "HGWGEDANL" of Sequence 2. In the example a gap is indicated by a "-".

Hypothetical Alignment Example:

```
Sequence 1:    ACMSHTWGER-NL          SEQ ID NO: 34
                   | ||| ||
Sequence 2:        HGWGEDANLAMNPS     SEQ ID NO: 35
```

For purposes of the present invention, the degree of identity between two nucleotide sequences is preferably determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

In a particular embodiment, the percentage of identity of an amino acid sequence of a polypeptide with, or to, amino acids 1 to 495 of SEQ ID NO: 32 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage. The percentage of identity to, or with, other sequences of the invention is calculated in an analogous way.

Host Cells

The host cell of the invention is a filamentous fungus. It is advantageous to use a host cell of the invention in recombinant production of a polypeptide of interest. The cell may be transformed with the DNA construct encoding the polypeptide of interest, conveniently by integrating the DNA construct in one or more copies into the host chromosome. This integration is generally considered to be an advantage as the DNA sequence is more likely to be stably maintained in the cell. Integration of the DNA construct into the host chromosome may be performed according to conventional methods, e.g., by homologous or heterologous recombination. Alternatively, the cell may be transformed with an expression vector as described in the examples below in connection with the different types of host cells.

Filamentous Fungal Host Cells

The host cell of the invention is a filamentous fungus represented by one of the following groups of Ascomycota, include, e.g., Neurospora, Eupenicillium (=Penicillium), Emericella (=Aspergillus), Eurotium (=Aspergillus).

In a preferred embodiment, the filamentous fungus belongs to one of the filamentous forms of the subdivision Eumycota and Oomycota as defined by Hawksworth et al., *In, Ainsworth and Bisby's Dictionary of The Fungi*, 8th edition, 1995, CAB International, University Press, Cambridge, UK. The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic.

In a more particular embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium*, and *Trichoderma* or a teleomorph or synonym thereof. In an even more particular embodiment, the filamentous fungal host cell is an *Aspergillus* cell. In another even more particular embodiment, the filamentous fungal host cell is an *Acremonium* cell. In another even more particular embodiment, the filamentous fungal host cell is a *Fusarium* cell. In another even more particular embodiment, the filamentous fungal host cell is a *Humicola* cell. In another even more particular embodiment, the filamentous fungal host cell is a *Mucor* cell. In another even more particular embodiment, the filamentous fungal host cell is a *Myceliophthora* cell. In another even more particular embodiment, the filamentous fungal host cell is a *Neurospora* cell. In another even more particular embodiment, the filamentous fungal host cell is a *Penicillium* cell. In another even more particular embodiment, the filamentous fungal host cell is a *Thielavia* cell. In another even more particular embodiment, the filamentous fungal host cell is a *Tolypocladium* cell. In another even more particular embodiment, the filamentous fungal host cell is a *Trichoderma* cell. In a most particular embodiment, the filamentous fungal host cell is an *Aspergillus awamori, Aspergillus foetidus, Aspergillus japonicus, Aspergillus aculeatus, Aspergillus niger, Aspergillus nidulans* or *Aspergillus oryzae* cell. In another particular embodiment, the filamentous fungal host cell is a *Fusarium* cell of the section Discolor (also known as the section *Fusarium*). For example, the filamentous fungal host cell may be a *Fusarium bactridioides, Fusarium cerealis, Fusarium crookwellense, Fusarium culmorum, Fusarium graminearum* (in the perfect state named *Gibberella zeae*, previously *Sphaeria*, synonym with *Gibberella roseum* and *Gibberella roseum* f.sp. *ceralis), Fusarium graminum, Fusarium heterosporum, Fusarium negundi, Fusarium reticulatum, Fusarium roseum, Fusarium sambucinum, Fusarium sarcochroum, Fusarium sulphureum, Fusarium trichothecioides* or *Fusarium venenatum* cell. In another preferred embodiment, the filamentous fungal host cell is a *Fusarium* strain of the section Elegans, e.g., *Fusarium oxysporum*. In another most particular embodiment, the filamentous fungal host cell is a *Humicola insolens* or *Humicola lanuginosa* cell. In another most particular embodiment, the filamentous fungal host cell is a *Mucor miehei* cell. In another most particular embodiment, the filamentous fungal host cell is a *Myceliophthora thermophilum* cell. In another most particular embodiment, the filamentous fungal host cell is a *Neurospora crassa* cell. In another most particular embodiment, the filamentous fungal host cell is a *Penicillium purpurogenum, Penicillium chrysogenum* or *Penicillium funiculosum* (WO 00/68401) cell. In another most particular embodiment, the filamentous fungal host cell is a *Thielavia terrestris* cell. In another most particular embodiment, the *Trichoderma* cell is a *Trichoderma harzianum, Trichoderma koningii, Trichoderma longibrachiatum, Trichoderma reesei* or *Trichoderma viride* cell.

In all embodiments of the invention the filamentous fungal host cell is a protease deficient or protease minus strain in which the expression of at least three endogenous proteases has been reduced or completely abolished.

In a particular embodiment the parent strain is the protease deficient *Aspergillus oryzae* strain BECh2 described in WO 00/39322, example 1, which is further referring to JaL228 described in WO 98/12300, example 1. This strain, which is alp⁻ and npI⁻ (deficient in the alkaline protease Alp and the neutral metalloprotease NpI) can be further modified to a particularly useful strain according to the invention, in which strain additional mutations have been introduced, as described in the following examples, to produce a filamentous fungal strain according to the invention, wherein additionally the serine protease of the subtilisin type designated PepC and optionally the calcium dependent, neutral, serine protease, KexB, are deficient.

Transformation of Filamentous Fungal Host Cells

Filamentous fungal host cells may be transformed by a process involving protoplast formation, transformation of the protoplasts, and regeneration of the cell wall in a manner known per se. Suitable procedures for transformation of *Aspergillus* host cells are described in EP 238 023, EP 184, 438, and Yelton et al., 1984, Proceedings of the National Academy of Sciences USA 81:1470-1474. A suitable method of transforming *Fusarium* species is described by Malardier et al., 1989, Gene 78:147-156 or in co-pending U.S. Ser. No. 08/269,449.

The filamentous fungal cells according to the invention are particularly useful for the expression of heterologous polypeptides.

In one aspect of the invention the filamentous fungal cells according to the invention are used for the expression of heterologous polypeptides. Thus one further aspect of the invention relates to a method for producing a heterologous polypeptide in a filamentous fungal host cell of the invention, comprising the steps:

(a) introducing into the host cell a nucleic acid sequence encoding the heterologous polypeptide;
(b) cultivating the cell from (a) in a suitable growth medium under conditions conducive for expression of the heterologous polypeptide; and
(c) isolating the protein product.

The heterologous polypeptide is in one embodiment a polypeptide of mammalian origin. Particularly the polypeptide is an antibody or an antibody fragment. In a further particular embodiment the antibody or antibody fragment is selected from the group consisting of IgG1, IgG2, IgG3, IgG4, IgM, IgA, IgD, IgE, F(ab')$_2$ and Fab.

Materials and Methods

Materials

Strains

*Aspergillus oryzae* IFO4177: available from Institute for fermentation, Osaka; 17-25 Juso Hammachi 2-Chome Yodogawa-Ku, Osaka, Japan. This strain is also equivalent to strain NBRC4177. The strain is therefore also available from NITE Biological Resource Center under the accession number NBRC4177.

JaL810 is described in example 3.

JaL893 is described in example 7.

JaL895 is described in example 7.

BECh2 is described in WO 00/39322, example 1, which is further referring JaL228 described in WO 98/12300, example 1.

NZ-2 is described in example 7.

HowB101 is described in WO 97/3556, example 1 is pyrG mutant of IFO4177.

JaL352 is described in example 2.

JaL355 is described in example 2.

JaL741 is described in example 7.

MT2874 is described in example 2.

ToC1418 is described in example 2.

JaL799 is described in example 10.

JaL827 is described in example 11.

Genes pyrG: This gene codes for orotidine-5'-phosphate decarboxylase, an enzyme involved in the biosynthesis of uridine.

Plasmids pBLSK-2-: The construction is described in Short et al, 1988, Nucleic acids Res. 16:7583-7600.

pCR04Blunt-TOPO is from Invitrogen A/S, Denmark.

pDV8 is described in patent WO 0168864, example 8 pNZ-3 is described in example 5.

pNZ-4 is described in example 6.

pIC7 is described in Marsh et al, 1984, Gene 32:481-485.

pJaL173 is described in patent WO 98/12300, example 1.

pJaL235 is described in WO 97/22705, example 1.

pJaL270 is described in example 1.

pJaL335 is described in patent WO 98/12300, example 1.

pJaL504 is described in example 1.

pJaL554 is described in example 9.

pJaL574 is described in example 9.

pJaL676 is described in WO 03/008575, example 5.

pJaL720 is described in example 4.

pJaL721 is described in WO 03/008575, example 17.

pJaL723 is described in example 4.

pJaL728 is described in example 4.

pJaL784 is described in example 4.

pJaL790 is described in example 4.

pJaL800 is described in example 9.

pJaL818 is described in example 9.

pJaL819 is described in example 9.

pJaL835 is described in example 9.

pJaL836 is described in example 9.

pMT2830 is described in example 1.

pMT2833 is described in example 1.

pMT2835 is described in example 1.

pSO2 is described in patent WO 9735956, example 1.

pUC19: The construction is described in Vieira et al, 1982, Gene 19:259-268.

Primers, DNA Sequences, and Amino Acid Sequences

Primer 419 (SEQ ID NO: 1)

Primer 424 (SEQ ID NO: 2)

Primer 423 SEQ ID NO: 3)

Primer 420 SEQ ID NO: 4)

Primer 104025 (SEQ ID NO: 5)

Primer 104027 (SEQ ID NO: 6)

Primer 104026 (SEQ ID NO: 7)

Primer 104028 (SEQ ID NO: 8)

Primer 108089 (SEQ ID NO: 9)

Primer 108091 (SEQ ID NO: 10)

Primer 114839 (SEQ ID NO: 11)

Primer 135944 (SEQ ID NO: 12)

Primer B6577F12 (SEQ ID NO: 13)

Primer B6575F12 (SEQ ID NO: 14)

Heavy chain (SEQ ID NO: 15)

Primer H-N (SEQ ID NO: 16)

Primer H-C (SEQ ID NO: 17)

Light chain (SEQ ID NO: 18)

Primer L-N (SEQ ID NO: 19)

Primer L-C (SEQ ID NO: 20)

Primer 172450 (SEQ ID NO: 21)

Primer 172449 (SEQ ID NO: 22)

Primer T5483H12 (SEQ ID NO 23)

Primer T5425G10 (SEQ ID NO 24)

Sal I fragment comprising kexB from *A. oryzae* IFO4177 (SEQ ID NO: 25)

alp cDNA (SEQ ID NO: 26)

npI cDNA (SEQ ID NO: 27)

pepC cDNA (SEQ ID NO: 28)

kexB cDNA (SEQ ID NO: 29)

Alp amino acid sequence (SEQ ID NO: 30)

NpI amino acid sequence (SEQ ID NO: 31)

PepC amino acid sequence (SEQ ID NO: 32)

KexB amino acid sequence (SEQ ID NO: 33)

Methods

General methods of PCR, cloning, ligation nucleotides etc. are well-known to a person skilled in the art and may for example be found in "Molecular cloning: A laboratory manual", Sambrook et al. (1989), Cold Spring Harbor lab., Cold Spring Harbor, N.Y.; Ausubel, F. M. et al. (eds.); "Current protocols in Molecular Biology", John Wiley and Sons, (1995); Harwood, C. R., and Cutting, S. M. (eds.); "DNA Cloning: A Practical Approach, Volumes I and II", D. N. Glover ed. (1985); "Oligonucleotide Synthesis", M. J. Gait ed. (1984); "Nucleic Acid Hybridization", B. D. Hames & S. J. Higgins eds (1985); "A Practical Guide To Molecular Cloning", B. Perbal, (1984).

DNA Hybridization

In short all DNA hybridisation was carried out for 16 hours at 65° C. in a standard hybridisation buffer of 10×Denhart's solution, 5×SSC, 0.02 M EDTA, 1% SDS, 0.15 mg/ml polyA RNA and 0.05 mg/ml yeast tRNA. After hybridisation the filters were washed in 2×SSC, 0.1% SDS at 65° C. twice and exposed to X-ray films.

PCR Amplification

All PCR amplifications was performed in a volume of 100 microL containing 2.5 units Taq polymerase, 100 ng of pSO2, 250 nM of each dNTP; and 10 pmol of each of the two primers described above in a reaction buffer of 50 mM KCl, 10 mM Tris-HCl pH 8.0, 1.5 mM $MgCl_2$. Amplification was carried out in a Perkin-Elmer Cetus DNA Termal 480, and consisted of one cycle of 3 minutes at 94° C., followed by 25 cycles of 1 minute at 94° C., 30 seconds at 55° C., and 1 minute at 72° C.

Example 1

Construction of the *Aspergillus oryzae* pepC Deletion Plasmid pMT2835

The single restriction endonuclease site BamHI and BglII in pDV8 was removed by two succeeding rounds of cutting with each of the restriction endonucleases and the free overhang-ends was filled out by treatment with Klenow polymerase and the four deoxyribonucleotides and ligated resulting in plasmid pJaL504.

Plasmid pJaL235 was digested with SalI and the 5912 bp fragment was re-ligated, resulting in plasmid pJaL270.

Based on the sequence previously determined for the pepC gene as cloned in pJaL270, the sequences flanking the pepC gene of *A. oryzae* were cloned from *A. oryzae* BECh2 by PCR. For amplification of the 5' flank, primers 419 and 424 were used (SEQ ID NO: 1 and 2) and for amplification of the 3' flank the primers used were 423 and 420 (SEQ ID NO: 3 and 4). The amplified flanks (0.8 kb and 1.1 kb, respectively) do not overlap with any of the pepC coding sequence. Primers 423 and 424 were designed to allow fusion of the two flanks by SOE and at the same time to introduce Nhe1 and Xho1 sites in the linker fusing the two flanks. The SOE fusion product was cloned into pCR®4-TOPO blunt to give pMT2830. The NheI and XhoI sites were used to insert the repeat flanked pyrG selection marker from pJaL335 which had previously been cloned in the HindIII site of pBLSK 2⁻ such that it could be moved as a Spe1-Xho1 fragment. The plasmid containing the pyrG insert was called pMT2833. Finally, the deletion cassette of pMT2833 containing the two pepC flanks on either side of the pyrG selection marker was transferred as a NotI-SpeI fragment into the NotI and XbaI sites of the tk counter selectable plasmid pJaL504 to give the deletion plasmid pMT2835. Note that pMT2835 contains a unique NotI site immediately downstream of the pepC 3' flank, which can be used to linearize the plasmid prior to transformation into *A. oryzae*.

Example 2

Construction of pepC Deleted *A. oryzae* Strain, MT2874

For removing the defect pyrG gene resident in the alkaline protease gene in the *A. oryzae* strain BECh2 the following was done:

A. Isolation of a pyrG Minus *A. oryzae* Strain, ToC1418

The *A. oryzae* strain BECh2 (alp minus and npI minus) was screened for resistance to 5-fluoro-orotic acid (FOA) to identify spontaneous pyrG mutants on minimal plates (Cove D. J. 1966. Biochem. Biophys. Acta. 113:51-56) supplemented with 1.0 M sucrose as carbon source, 10 mM sodiumnitrate as nitrogen source, and 0.5 mg/ml FOA. One strain, ToC1418, was identified as being pyrG minus. ToC1418 is uridine dependent, therefore it can be trans-formed with the wild type pyrG gene and transformants selected by the ability to grow in the absence of uridine.

B. Construction of a pyrG Plus *A. oryzae* Strain, JaL352.

The mutation in the defect pyrG gene resident in the alkaline protease gene was determined by sequencing. Chromosomal DNA from *A. oryzae* strain BECh2 was prepared and a 933 bp fragment was amplified containing the coding region of the defect pyrG gene by PCR with primers 104025 (SEQ ID NO: 5) and 104026 (SEQ ID NO: 7). The 933 bp fragment was purified and sequenced with the following primers: 104025, 104026, 104027 (SEQ ID NO: 6), 104028 (SEQ ID NO: 8), 108089 (SEQ ID NO: 9), and 108091 (SEQ ID NO: 10). Sequencing shows that an extra base, a G, was inserted at position 514 in the pyrG-coding region (counting from the A in the start codon of the pyrG gene), thereby creating a frame-shift mutation.

In order to recreate a wild type pyrG gene from the defect pyrG gene resident in the alkaline protease gene, alp, the *A. oryzae* pyrG minus strain ToC1418 was transformed with 150 pmol of oligo-nucleotide 114839 (SEQ ID NO: 11) phosphorylated in the 5' end, using standard procedures. The oligo-nucleotide restores the pyrG reading frame, but at the same time a silence mutation is introduce thereby creating a StuI restriction endonuclease site. Transformants were then selected by their ability to grow in the absence of uridine on minimal plates (Cove D. J. 1966. Biochem. Biophys. Acta. 113:51-56) supplemented with 1.0 M sucrose as carbon source, and 10 mM sodiumnitrate as nitrogen source. After re-isolation chromosomal DNA was prepared from 8 transformants. To confirm the changes a 785 bp fragment was amplified by PCR with the primers 135944 (SEQ ID NO: 12) and 108089 (SEQ ID NO: 9), which is covering the region of interest. The 785 bp fragment was purified and sequenced with the primers 108089 (SEQ ID NO: 9) and 135944 (SEQ ID NO: 12). One strain having the expected changes was named JaL352.

C. Isolation of a pyrG Minus *A. oryzae* Strain, JaL355

For removing the pyrG gene resident in the alkaline protease gene JaL352 was trans-formed by standard procedure with the 5.6 kb BamHI fragment of pJaL173 harboring the 5' and 3' flanking sequence of the *A. oryzae* alkaline protease gene. Protoplasts were regenerated on non-selective plates and spores were collected. About 109 spores were screened for resistance to FOA to identify pyrG mutants. After re-isolation chromosomal DNA was prepared from 14 FOA resistance transformants. The chromosomal DNA was digested with Bal I and analysed by Southern blotting, using the 1 kb 32P-labelled DNA Bal I fragment from pJaL173 containing part of the 5' and 3' flanks of the *A. oryzae* alkaline protease gene as the probe. Strains of interest were identified by the disappearance of a 4.8 kb Bal I band and the appearance of a 1 kb Bal I band. Probing the same filter with the 3.5 kb 32P-labelled DNA Hind III fragment from pJaL335 containing the *A. oryzae* pyrG gene shows that the 4.8 kb Bal I band has disappeared in the strains of interest. One strain resulting from these transformants was named JaL355.

D. Construction of pepC Deleted *A. oryzae* Strain, MT2874

20 microgram of pMT2835 was cut with NotI and subsequently the enzyme was heat inactivated as recommended by the manufacturer (New England Biolabs). The plasmid was then ethanol precipitated and re-dissolved in Tris buffer (10 mM pH 8.0) at a concentration suitable for transformation into *Aspergillus oryzae*.

The linearized plasmid DNA was transformed into *Aspergillus oryzae* JaL355 with selection for pyrG and counter selection of the tk gene on FDU plates as previously described in WO 0168864. 24 transformant colonies were twice re-isolated and finally grown up in liquid medium (YPD). Chromosomal DNA was prepared as previously described in WO 0168864, and used for Southern analysis of the pepC locus with the aim to identify transformants in which a clean double cross-over between the chromosomal pepC and the deletion cassette had occurred. The chromosomal DNA was digested with EcoRI and PvuI. The Southern blot was first probed with the 5' flank excised as a 0.8 kb EcoRI-XhoI fragment from pMT2835 (Probe1). For an intact wt pepC locus, a 3.1 kb EcoRI-PvuI fragment is expected to hybridize to this probe, while for the pepC deleted derivative originating from the desired double crossover a 5.5 kb fragment will hybridize. Only one out of the 24 transformants, JaL355/pMT2835#5, showed both the disappearance of the 3.1 kb hybridizing fragment and the appearance of the 5.5 kb hybridizing fragment in a Southern blot analysis. The Southern was stripped of the first 5' flank probe and re-probed with a 3' flank probe excised as a 1.1 kb EcoRI fragment from pMT2835 (Probe 2). For the wt pepC locus a 3.1 kb is again expected to hybridize to this fragment while for the pepC deletion strain originating from the desired cross over it is expected that a 1.1 kb fragment will hybridize. Again only one of the 24 transformants, JaL355/pMT2835#5, showed both the disappearance of the 3.1 kb hybridizing fragment and the appearance of the 1.1 kb hybridizing fragment in a Southern blot analysis. The filter was again stripped and re-probed with a third probe. The third probe was excised as a 0.7 kb Asp718-PstI fragment from pJaL270 (Probe3). This fragment is part of the pepC coding sequence itself. This third probe is again expected to hybridize to a 3.1 kb EcoRI-PvuI fragment of the wt pepC locus while no hybridization signal is expected from the desired pepC deleted derivative. A few transformant strains including JaL355/pMT2835#5 failed to hybridize to the third probe.

In conclusion, of the 24 transformant only JaL355/pMT2835#5 contains the desired clean double cross over leading to a deletion of the pepC coding sequence. JaL355/pMT2835#5 was preserved as *A. oryzae* strain MT2874. The pepC deleted strain MT2874 does appear to have slightly changed colony morphology and sporulation proficiency relative to the parent strain. In particular sporulation at elevated temperature e.g. 37 degrees C. seems poor.

Example 3

Construction of a pepC Deleted *A. oryzae* Strain, JaL810 (A1560-ΔpepC)

Clean pepC disruptions were made in *A. oryzae* strain HowB101. The procedures for making and verifying the deletion is identical to those described in example 2, sections D.

Example 4

Construction of *Aspergillus* Expression Plasmid pJaL790

The *Aspergillus* expression plasmid pJaL790, suitable for expressing a gene of interest under the control of the *A. niger* neutral amylase promoter (NA2) was constructed in the following way:

The single restriction endonuclease site HindIII in the vector pUC19 was removed by cutting with HindIII and the free overhang-ends was filled out by treatment with Klenow polymerase and the four deoxyribonucleotides and ligated, resulting in plasmid pJaL720. The 1140 bp EcoRI-BamHI fragment from pJaL721, containing the double *A. niger* NA2 promoter, was cloned into the corresponding sites in pJaL720, resulting in pJaL723. A 537 bp fragment was amplified by PCR with pJaL676 as template and the primers B6577F12 (SEQ ID NO: 13) and B6575F12 (SEQ ID NO: 14). This was digested with EcoRI, the free overhang-ends were filled in by treatment with Klenow polymerase and the four deoxyribonucleotides and the resulting 524 bp fragment was cloned into the HindIII site, which was blunt ended in pJaL723, giving plasmid pJaL728. The single restriction endonuclease site HindIII in the vector pJaL728 was removed by cutting with HindIII and the free overhang-ends was filled in by treatment with Klenow polymerase and the four deoxyribonucleotides and ligated, resulting in plasmid pJaL784. A 1671 bp EcoRI-BamHI fragment from pJaL784 was ligated to the 5735 bp EcoRI-BamHI fragment from pJaL721, resulting in pJaL790.

Example 5

Construction of a native IgG1 Heavy-Chain *Aspergillus* Expression Plasmid

A human IgG1 heavy chain encoding sequence was amplified by PCR using SEQ ID NO: 15 as template and the forward primer H-N (SEQ ID NO:16) and the reverse primer H-C (SEQ ID NO:17). Primers H-N and H-C introduce a BamHI and XhoI restriction site upstream of the translational start codon and after the translation termination signal, respectively, for cloning purposes. The PCR product on 1431 bp was purified and cut with the restriction endonucleases BamHI and XhoI. The resulting 1419 bp fragment was cloned into the corresponding site in pJaL790 to create pNZ-3. DNA from clone pNZ-3 was sequenced to check that it was the right sequence.

Example 6

Construction of a Native IgG Kappa Light-Chain *Aspergillus* Expression Plasmid

A human IgG kappa light-chain encoding sequence was amplified by PCR using SEQ ID NO: 18 as template and with the forward primer L-N (SEQ ID NO:19) and the reverse primer L-C (SEQ ID NO: 20). Primers L-N and L-C introduce a BamHI and XhoI restriction site upstream the translational start codon and after the translation termination signal, respectively, for cloning purposes. The PCR product of 732 bp was purified and cut with the restriction endonucleases BamHI and XhoI. The resulting 720 bp fragment was cloned into the corresponding site in pJaL790 to create pNZ-4. DNA from clone pNZ-4 was sequenced to check that it was the right sequence.

Example 7

Expression of IgG1 Antibody in *Aspergillus oryzae*

The strains MT2874, BECh2, IFO4177, and JaL810 was transformed with a one to one ratio of the expression plasmid pNZ-3, and pNZ-4 as described by Christensen et al.; Biotechnology 1988, 6:1419-1422. In short, *A. oryzae* mycelia were grown in a rich nutrient broth. The mycelia were separated from the broth by filtration. The enzyme preparation Novozyme® (Novo Nordisk) was added to the mycelia in osmotically stabilizing buffer such as 1.2 M $MgSO_4$ buffered to pH 5.0 with sodium phosphate (alternatively other enzyme mixes such as e.g. Glucanex® 200G can be used). The suspension was incubated for 60 minutes at 37 degrees C. with agitation. The protoplast was filtered through mira-cloth to remove mycelial debris. The protoplast was harvested and washed twice with STC (1.2 M sorbitol, 10 mM $CaCl_2$, 10 mM Tris-HCl pH 7.5). The protoplasts were finally re-suspended in 200-1000 microl STC.

For transformation, 5 microg DNA was added to 100 microl protoplast suspension and then 200 microl PEG solution (60% PEG 4000, 10 mM $CaCl_2$, 10 mM Tris-HCl pH 7.5) was added and the mixture is incubated for 20 minutes at room temperature. The protoplast were harvested and washed twice with 1.2 M sorbitol. The protoplast was finally re-suspended 200 microl 1.2 M sorbitol. Transformants containing the amdS gene, present on pNZ-3 or pNZ-4, were selected on minimal plates (Cove D. J. 1966. Biochem. Biophys. Acta. 113:51-56) containing 1.0 M sucrose as carbon source, 10 mM acetamide as nitrogen source, 15 mM CsCl to inhibit background growth, and 250 mM 5-ALA. After 4-5 days of growth at 37 degrees C., stable transformants appeared as vigorously growing and sporulating colonies. Transformants were purified twice through conidiospores.

Shake flask containing 10 ml YPM medium (2 g/l yeast extract, 2 g/l peptone, and 2% maltose) was inoculated with spores from the transformants from the 3 strains and incubated at 30 degrees C., 200 rpm for 4 days.

The supernatants were screened for intact IgG1 by ELISA (Harlow, E. and Lane, D., Antibodies: A Laboratory Manual. Cold Spring Harbor Laboratory Press, (New York, 1988), p. 579). Intact IgG was determined using an ELISA which uses goat anti-human IgG (Fc specific) as the capture antibody and goat anti-human kappa chain conjugated with alkaline phosphatase as the detection antibody. As standard was used a human myeloma IgG1, kappa purified from human plasma. The ELISA procedure was a standard protocol.

One transformant (containing both expression plasmids pNZ-3 and pNZ-4) from each parent strain MT2874, BECh2, IFO4177 and JaL810, producing intact IgG1, was selected and preserved as *A. oryzae* strain JaL741, NZ-2, JaL893 and JaL895, respectively.

Example 8

Production and Characterization of IgG1 from *Aspergillus oryzae*

The transformed *A. oryzae* strains JaL741, NZ-2, JaL893, and JaL895 were grown in a fermentor using standard substrate and after 5 days of incubation the fermentation broth was harvested. The whole broth was centrifuged and the supernatant passed through a 0.22 μm PES filter membrane (Corning).

MEP HyperCel Column

The filter flow through was loaded on a MEP HyperCel column (BioSepra) on an ÄKTA explorer system (Amersham Biosciences). The column was washed with 50 mM HEPES pH 7.5 followed by 25 mM Caprylate in 50 mM Tris-HCl pH 8. IgG1 was eluted with 50 mM MES pH 5.5.

Protein A Column

Eluted IgG1 from the MEP HyperCel column was adjusted to pH 7 with 1M Tris base and loaded on a nProtein A Sepharose 4 Fast Flow column (Amersham Biosciences) on an ÄKTA explorer system (Amersham Biosciences). The column was washed with 20 mM Na-Phosphate pH 7. IgG1 was eluted with 100 mM Citric acid pH 4.

IgG Characterisation

Purified IgG1 samples were analysed by SDS-PAGE on 4-20% Tris-glycine gels under reducing and non-reducing conditions. Protein bands were identified by N-terminal sequencing. For N-terminal sequencing gels were blotted to a PVDF membrane that was stained with coomassie blue. Protein bands were cut out from the blot and applied directly to a Precise protein sequencer (Applied Biosystems).

Intact IgG in the starting material as well as in the purified fractions was quantified as described in example 7.

SDS-Gel Analysis

The produced IgG was analysed on SDS-gels in order to characterize the products in terms of degree of degradation.

In NZ-2 (Bech2 with IgG produced from pNZ-3 and pNZ-4) substantial antibody heavy chain degradation was observed with several fragments appearing on SDS-PAGE as further identified by N-terminal sequencing. Cleavage was not sequence specific but was found in less structured linker regions of the heavy chain.

In JaL741 (MT2874 with IgG produced from pNZ-3 and pNZ-4) significantly reduced levels of heavy chain degradation was observed compared to what was found in the NZ-2 product. Cleavage was found to be sequence specific with cleavage after the one Lys-Arg site of the heavy chain sequence. Lys-Arg sites are known to be targets for the site specific KexB protease of *Aspergillus oryzae* cleaving only the carboxyl side of Lys-Arg and Arg-Arg.

Before PepC inactivation the site specific degradation, possibly due to kexB, was obscured.

In JaL893 (IFO4177 with IgG produced from pNZ-3 and pNZ-4) a very substantial antibody heavy chain degradation was observed with several fragments appearing on SDS-PAGE as further identified by N-terminal sequencing. Cleavage was not sequence specific but was found in less structured linker regions of the heavy chain.

In JaL895 (JaL810 with IgG produced from pNZ-3 and pNZ-4) a very substantial anti-body heavy chain degradation was observed with several fragments appearing on SDS-PAGE as further identified by N-terminal sequencing. Cleavage was not sequence specific but was found in less structured linker regions of the heavy chain. This shows that deletion of the pepC protease alone is not enough for reducing the heavy chain degradation.

Example 9

Construction of the *Aspergillus oryzae* kexB Deletion Plasmid pJaL836

From plasmid pSO2, which encode the *A. oryzae* ISO4177 pyrG gene, a 5336 bp SpeI-SspBI fragment and a 316 bp Asp718-NheI fragment (part of the pyrG promoter) were purified and ligated resulting in plasmid pJaL554. The 316 bp fragment was cloned downstream of the encoded pyrG gene, thereby creating a pyrG gene which is flanked by a repeated sequence of 316 bp.

From pJaL504 a 2514 bp fragment were amplified by PCR with primer 172450 and 172449 (SEQ ID NO: 21 and 22) and cloned into the vector pCR®4Blunt-TOPO resulting in plasmid pJaL574.

From pJaL574 a 2587 bp fragment were amplified by PCR with primer T5483H12 and T5425G10 (SEQ ID NO: 23 and 24). This fragment was restriction digested with HindIII and NdeI resulting in a 2582 bp fragment, which was cloned into the corresponding site in the vector pUC19 resulting in plasmid pJaL835.

Plasmid pJaL800 contains a 6968 bp SalI fragment from *A. oryzae* IFO4177 encoding the kexB gene (SEQ ID NO: 25) in pUC19. A 4658 BglII fragment from pJaL800 were subcloned into the BglII site of the vector pIC7 resulting in pJaL818. The repeat flanked pyrG selection marker from pJaL554 were moved as a 2313 bp SmaI fragment and cloned into the BalI site of pJaL818 resulting in plasmid pJaL819.

The pyrG gene replaces thereby a 911 bp BalI encoding part of the kexB gene and the pyrG gene is then flanked by a 1292 bp fragment of the 5' end of kexB and a 2455 bp fragment of the 3' end of kexB. Finally, the deletion cassette of pMT2833 containing the two pepC flanks on either side of the pyrG selection marker was transferred as a 4063 bp EcoRI fragment into the EcoRI sites of the tk counter selectable plasmid pJaL835 to give the deletion plasmid pJaL836. Note that pJaL836 contains a unique NotI site immediately downstream of the kexB 5' flank, which can be used to linearize the plasmid prior to transformation into A. oryzae.

Example 10

Construction of pepC and kexB Deleted A. oryzae Strain, JaL799 (JaL763-ΔkexB)

A. Isolation of a MT2874 pyrG Minus Strain, JaL763 (alp Minus, npI Minus, pepC Minus)

The A. oryzae strain MT2874 was screened for resistance to 5-fluoro-orotic acid (FOA) to identify spontaneous pyrG mutants on minimal plates (Cove D. J. 1966. Biochem. Biophys. Acta. 113:51-56) supplemented with 1.0 M sucrose as carbon source, 10 mM sodiumnitrate as nitrogen source, and 0.5 mg/ml FOA. One strain, ToC1418, was identifying as being pyrGminus. JaL763 is uridine dependent, therefore it can be transformed with the wild type pyrG gene and transformants selected by the ability to grow in the absence of uridine.

B. Construction of pepC and KexB Deleted A. oryzae Strain, JaL799.

20 microgram of pJaL836 was cut with NotI and subsequently the enzyme was heat inactivated as recommended by the manufacturer (New England Biolabs). The plasmid was then ethanol precipitated and re-dissolved in Tris buffer (10 mM pH 8.0) at a concentration suitable for transformation into Aspergillus oryzae.

The linearized plasmid DNA was transformed into Aspergillus oryzae JaL763 with selection for pyrG and counter selection of the tk gene on FDU plates as previously described in WO 0168864. Transformant colonies were twice re-isolated and finally grown up in liquid medium (YPD). Chromosomal DNA was prepared as previously described in WO 0168864, and used for Southern analysis of the kexB locus with the aim to identify transformants in which a clean double cross-over between the chromosomal kexB and the deletion cassette had occurred. The chromosomal DNA was digested with BglII and BglII-HindIII. The Southern blot was first probed with the 5' flank excised as a 1292 kb BglII-MIuNI fragment from pJaL818 (Probe1). For the wt intact kexB locus, a 4.6 kb BglII fragment is expected to hybridize to this probe for both the BglII and the BglII-HindIII digestion, while for the kexB deleted derivative originating from the desired double cross-over a 6.0 kb fragment and a 1.3 kb fragment will hybridize, respectively. The Southern was stripped of the first 5' flank probe and re-probed with a probe excised as a 0.8 kb MIuNI fragment of pJaL818 (Probe 2). For the wt kexB locus a 4.6 kb fragment was again shown to hybridize to this fragment for both digestions, while for the kexB deletion strain originating from the desired cross over no hybridization was obtained. A strain with the above characteristics was preserved as A. oryzae strain JaL799 (JaL763-ΔkexB).

Example 11

Expression of IgG1 Antibody in A. oryzae JaL799

The strain JaL799 was transformed with expression plasmids pNZ-3, and pNZ-4, and a transformant was selected, as described in example 7, and named JaL827.

The resulting IgG produced from JaL827 was characterized as described in example 8. In JaL827 (JaL799 with IgG produced from pNZ-3 and pNZ-4) significantly reduced levels of heavy chain degradation was observed compared to what was found in JaL741 (example 8). In JaL741 the major protein bands observed were found to be the result of sequence specific degradation with cleavage after the one Lys-Arg site of the heavy chain sequence. In contrast to this, in JaL827 none of this sequence specific degradation was seen and the minor bands were found to be the result of unspecific degradation. The result was that less degradation products were seen from JaL827.

The invention claimed is:

1. A filamentous fungal cell in which an endogenous alkaline protease gene encoding a polypeptide having alkaline protease activity and having an amino acid sequence which has at least 85% identity to the amino acid sequence of SEQ ID NO:30, an endogenous neutral metalloprotease gene encoding a polypeptide having neutral metalloprotease activity and having an amino acid sequence which has at least 85% identity to the amino acid sequence of SEQ ID NO:31, an endogenous serine protease gene encoding a polypeptide having serine protease activity and having an amino acid sequence which has at least 85% identity to the amino acid sequence of SEQ ID NO:32, and an endogenous intracellular kexin maturase gene encoding a polypeptide having kexin maturase activity and having an amino acid sequence which has at least 85% identity to the amino acid sequence of SEQ ID NO:33 have been inactivated, whereby the cell expresses undetectable levels of alkaline protease, neutral metalloprotease, serine protease, and kexin maturase polypeptides or expresses functionally inactive alkaline protease, neutral metalloprotease, serine protease, and kexin maturase polypeptides.

2. The filamentous fungal cell according to claim 1, wherein the alkaline protease polypeptide is encoded by the alp gene, the neutral metalloprotease polypeptide is encoded by the npI gene, the serine protease polypeptide is encoded by the pepC gene, and the kexin maturase polypeptide is encoded by the kexB gene.

3. The filamentous fungal cell according to claim 2, which has the phenotype alp⁻, npI⁻, pepC⁻, and kexB⁻, wherein the alp gene comprises a polypeptide-encoding nucleotide sequence which has at least 90% identity to the nucleic acid sequence of SEQ ID NO:26, the npI gene comprises a polypeptide-encoding nucleotide sequence which has at least 90% identity to the nucleic acid sequence of SEQ ID NO:27, the pepC gene comprises a polypeptide-encoding nucleotide sequence which has at least 90% identity to the nucleic acid sequence of SEQ ID NO:28, and the kexB gene comprises a polypeptide-encoding nucleotide sequence which has at least 90% identity to the nucleic acid sequence of SEQ ID NO:29.

4. The filamentous fungal cell according to claim 1, wherein the fungal cell is chosen from the group consisting of the genera *Aspergillus, Acremonium, Fusarium, Humicola, Mucor, Myceliophthora, Neurospora, Penicillium, Thielavia, Tolypocladium*, and *Trichoderma*.

5. The filamentous fungal cell according to claim 4, wherein the *Aspergillus* comprises *Aspergillus awamori, Aspergillus foetidus, Aspergillus japonicus, Aspergillus aculeatus, Aspergillus niger, Aspergillus nidulans* or *Aspergillus oryzae*.

6. A method for producing a heterologous polypeptide in the filamentous fungal host cell according to claim 1, comprising
   (a) introducing into the host cell a nucleic acid sequence encoding the heterologous polypeptide;
   (b) cultivating the cell from (a) in a suitable growth medium under conditions conducive for expression of the heterologous polypeptide; and
   (c) isolating the heterologous polypeptide product.

7. The method according to claim 6, wherein the heterologous polypeptide is a mammalian polypeptide.

8. The method according to claim 7, wherein the polypeptide is an antibody or an antibody fragment.

9. The method according to claim 8, wherein the antibody or antibody fragment is selected from the group consisting of IgG1, IgG2, IgG3, IgG4, IgM, IgA, IgD, IgE, F(ab'), and Fab.

10. The method according to claim 9, wherein the antibody is IgG1.

* * * * *